US 9,226,748 B2

(12) United States Patent
Levine et al.

(10) Patent No.: US 9,226,748 B2
(45) Date of Patent: Jan. 5, 2016

(54) SURGICAL SUTURING DEVICE, METHOD AND TOOLS USED THEREWITH

(75) Inventors: David E. Levine, Devon, PA (US);
Daniel S. Levine, Wayne, PA (US);
Marshall S. Levine, Wayne, PA (US);
Neal B. Cohen, Flourtown, PA (US)

(73) Assignee: Alpha Scientific Corporation, Exton, PA (US)

( * ) Notice: Subject to any disclaimer, the term of this patent is extended or adjusted under 35 U.S.C. 154(b) by 638 days.

(21) Appl. No.: 12/384,326

(22) Filed: Apr. 2, 2009

(65) Prior Publication Data

US 2009/0216251 A1  Aug. 27, 2009

Related U.S. Application Data

(63) Continuation-in-part of application No. PCT/US2008/009012, filed on Jul. 25, 2008.

(60) Provisional application No. 60/962,031, filed on Jul. 26, 2007.

(51) Int. Cl.
*A61B 17/04* (2006.01)
*A61B 17/00* (2006.01)
*A61B 17/06* (2006.01)

(52) U.S. Cl.
CPC ......... *A61B 17/0485* (2013.01); *A61B 17/0482* (2013.01); *A61B 2017/00792* (2013.01); *A61B 2017/0496* (2013.01); *A61B 2017/06052* (2013.01); *A61B 2017/06176* (2013.01)

(58) Field of Classification Search
CPC ........... A61B 17/0485; A61B 17/0482; A61B 2017/06176; A61B 2017/0496; A61B 2017/00792; A61B 2017/06052
See application file for complete search history.

(56) References Cited

U.S. PATENT DOCUMENTS

| 669,034 A | 2/1901 | Manly |
| 755,921 A | 3/1904 | O'Neill |
| 2,665,692 A | 1/1954 | L'esperance |
| 3,739,784 A | 6/1973 | Itoh |

(Continued)

FOREIGN PATENT DOCUMENTS

| EP | 1 598 017 A1 | 11/2005 |
| EP | 1 862 125 A2 | 12/2007 |

(Continued)

OTHER PUBLICATIONS

Office Action issued Jan. 14, 2014 in JP Application No. 2012-503414.

(Continued)

*Primary Examiner* — Gregory Anderson
*Assistant Examiner* — Son Dang
(74) *Attorney, Agent, or Firm* — Panitch Schwarze Belisario & Nadel LLP

(57) ABSTRACT

A suture insertion device is provided for positioning a suture inside a layer of subcutaneous tissue from a remote access point. A tether insertion device is provided for positioning a tether within subcutaneous tissue for operating on the suture from a remote access point. The suture insertion device and the tether insertion device cooperate to form the suture into a tissue-supporting sling useful for performing various surgical procedures, including but not limited to plastic surgery such as mid face lifts, neck lifts, brow lifts, under eye lifts, breast lifts, and organ repositioning.

61 Claims, 31 Drawing Sheets

(56) References Cited

U.S. PATENT DOCUMENTS

| | | |
|---|---|---|
| 3,903,892 A | 9/1975 | Komiya |
| 3,910,279 A | 10/1975 | Okada et al. |
| 4,306,561 A | 12/1981 | de Medinaceli |
| 4,312,337 A | 1/1982 | Donohue |
| 4,635,636 A | 1/1987 | Goldstein |
| 4,638,802 A | 1/1987 | Okada |
| 4,655,223 A | 4/1987 | Kim |
| 5,224,488 A | 7/1993 | Neuffer |
| 5,318,578 A | 6/1994 | Hasson |
| 5,569,271 A | 10/1996 | Hoel |
| 5,624,446 A | 4/1997 | Harryman, II |
| 5,645,548 A | 7/1997 | Augsburger |
| 5,707,379 A | 1/1998 | Fleenor et al. |
| 5,759,188 A | 6/1998 | Yoon |
| 5,766,217 A | 6/1998 | Christy |
| 5,776,150 A | 7/1998 | Nolan et al. |
| 5,782,845 A | 7/1998 | Shewchuk |
| 5,807,276 A | 9/1998 | Russin |
| 5,810,861 A | 9/1998 | Gaber |
| 6,030,391 A | 2/2000 | Brainard et al. |
| 6,036,700 A | 3/2000 | Stefanchik et al. |
| 6,200,327 B1 | 3/2001 | Assal |
| 6,638,286 B1 * | 10/2003 | Burbank et al. ............... 606/157 |
| 6,746,471 B2 | 6/2004 | Mortier et al. |
| 6,749,615 B2 | 6/2004 | Burdulis et al. |
| 6,770,084 B1 | 8/2004 | Bain et al. |
| 6,835,193 B2 | 12/2004 | Epstein et al. |
| 6,936,024 B1 | 8/2005 | Houser |
| 7,101,378 B2 | 9/2006 | Salameh et al. |
| 7,198,626 B2 | 4/2007 | Lee et al. |
| 7,264,623 B2 | 9/2007 | Harris, Jr. et al. |
| 7,322,939 B2 | 1/2008 | Burbank et al. |
| 7,615,062 B2 | 11/2009 | Deland |
| 7,771,441 B2 | 8/2010 | Cerundolo |
| 7,918,868 B2 * | 4/2011 | Marshall et al. ............... 606/144 |
| 7,955,341 B2 | 6/2011 | Cerundolo |
| 8,353,920 B2 | 1/2013 | Mikkaichi |
| 2001/0025171 A1 | 9/2001 | Mortier et al. |
| 2004/0102809 A1 | 5/2004 | Anderson |
| 2004/0133216 A1 | 7/2004 | Wulc et al. |
| 2004/0267270 A1 | 12/2004 | Jacobs et al. |
| 2005/0261581 A1 | 11/2005 | Hughes et al. |
| 2006/0004409 A1 | 1/2006 | Nobis et al. |
| 2006/0004410 A1 | 1/2006 | Nobis et al. |
| 2006/0025819 A1 | 2/2006 | Nobis et al. |
| 2006/0069398 A1 | 3/2006 | Suzuki et al. |
| 2006/0217762 A1 | 9/2006 | Maahs et al. |
| 2006/0282100 A1 | 12/2006 | Pasricha et al. |
| 2007/0118174 A1 | 5/2007 | Chu |
| 2007/0179509 A1 | 8/2007 | Nagata et al. |
| 2007/0293876 A1 | 12/2007 | Abe et al. |
| 2008/0172085 A1 | 7/2008 | Chiu et al. |
| 2009/0062817 A1 | 3/2009 | Suzuki et al. |
| 2009/0082797 A1 | 3/2009 | Fung et al. |
| 2009/0216251 A1 | 8/2009 | Levine et al. |
| 2010/0137679 A1 | 6/2010 | Lashinski et al. |
| 2010/0331612 A1 | 12/2010 | Lashinski et al. |
| 2012/0143225 A1 | 6/2012 | Chin et al. |

FOREIGN PATENT DOCUMENTS

| | | |
|---|---|---|
| JP | S63-40559 A | 2/1988 |
| JP | H06-74146 U | 10/1994 |
| JP | H10-216161 A | 8/1998 |
| JP | 2001-198131 A | 7/2001 |
| JP | 2002-028164 A | 1/2002 |
| JP | 04513702 | 5/2004 |
| JP | 2004-526483 A | 9/2004 |
| JP | 3628597 B2 | 3/2005 |
| JP | 2007151615 | 6/2007 |
| JP | 2007-167500 A | 7/2007 |
| JP | 2007-296319 A | 11/2007 |
| WO | 9406357 A1 | 3/1994 |
| WO | 9531149 A1 | 11/1995 |
| WO | 9602197 A1 | 2/1996 |
| WO | 9835616 A1 | 8/1998 |
| WO | 02039905 | 5/2002 |
| WO | 03077771 A1 | 9/2003 |
| WO | 2005096956 A1 | 10/2005 |
| WO | 2006047563 A2 | 5/2006 |
| WO | 2007073931 A1 | 7/2007 |
| WO | 2008042992 A2 | 4/2008 |
| WO | 2008070691 A2 | 6/2008 |
| WO | WO 2009045248 | 4/2009 |

OTHER PUBLICATIONS

Partial translation of an Office Action issued Mar. 11, 2014 in MX Application No. MX/a/2010/001019.
EP Extended Search Report in EP Application No. 10759139.8 dated Jul. 15, 2013, 8 pages.
Office Action issued Jul. 31, 2014 in AU Application No. 2010232964.
Office Action issued Jul. 31, 2014 in AU Application No. 2013204680.
Office Action issued Aug. 15, 2014 in AU Application No. 2013204057.
Int'l Search Report and Written Opinion issued Aug. 28, 2014 in Int'l Application No. PCT/US2014/030533.
Office Action issued Jul. 10, 2014 in CA Application No. 2,694,650.
Office Action issued Oct. 16, 2014 in U.S. Appl. No. 12/452,743 by Levine.
Office Action issued Oct. 1, 2014 in IL Application No. 215256.
English translation of an Office Action issued Oct. 14, 2014 in MX Application No. MX/a/2010/001019.
Office Action issued Oct. 29, 2014 in KR Application No. 10-2010-7003741.
Office Action issued Jan. 27, 2015 in JP Application No. 2014-002445.
Int'l Preliminary Report on Patentability issued Feb. 6, 2015 in Int'l Application No. PCT/US2014/030533.
Office Action issued May 29, 2015 in U.S. Appl. No. 12/452,743 by Levine.
Search Report issued Mar. 27, 2015 in EP Applicaiton No. 08836569.7.
Office Action issued May 4, 2015 in IL Application No. 226164.
Office Action issued May 21, 2015 in CA Application No. 2,694,650.
English translation of an Office Action issued in MX Application No. MX/a/2010/001019.

\* cited by examiner

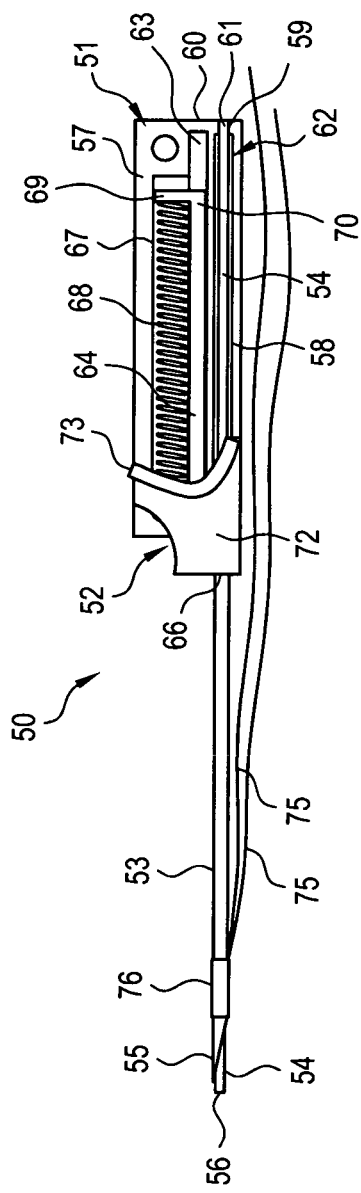
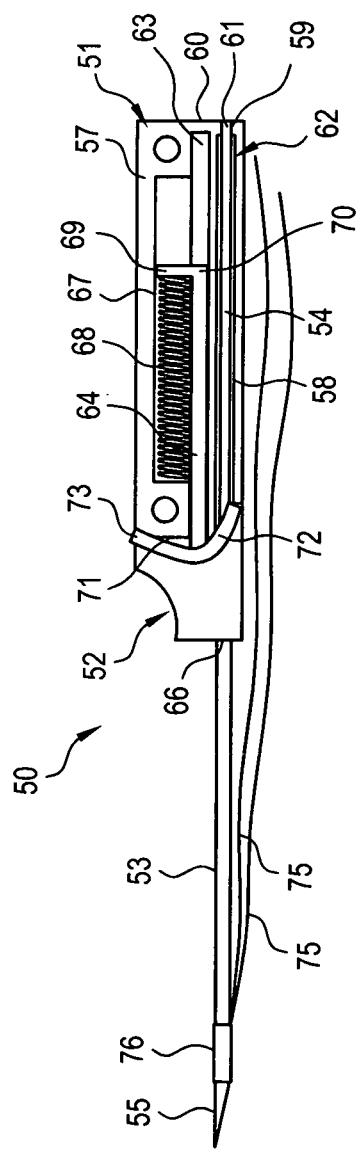
Fig. 7
Fig. 8

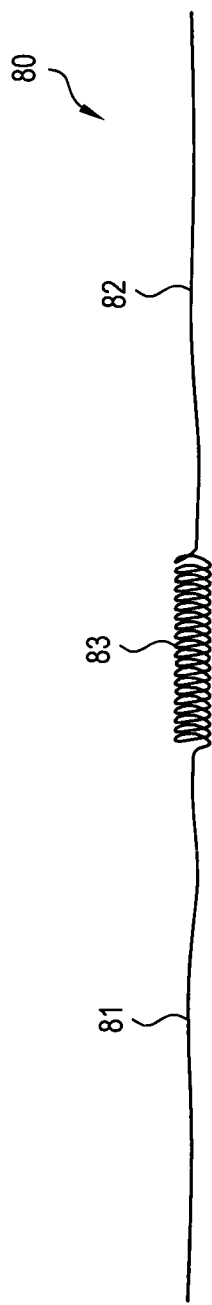
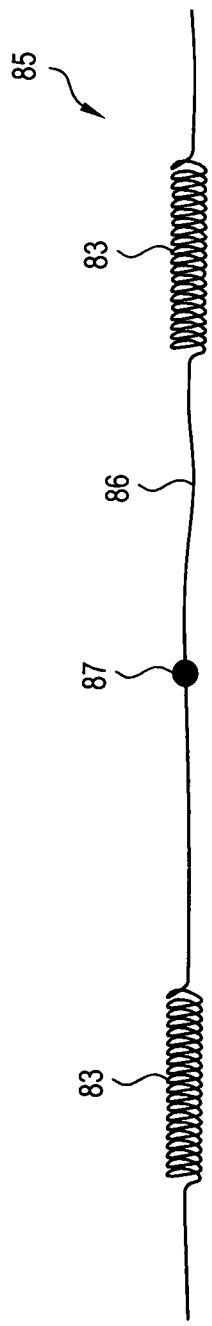

SURGICAL SUTURING DEVICE, METHOD AND TOOLS USED THEREWITH

RELATED CASES

This application is a continuation-in-part of prior, International Application No. PCT/US2008/009012, which designates the United States, having an International Filing Date of Jul. 25, 2008. International Application No. PCT/US2008/009012 claims the benefit and priority of U.S. Provisional Application No. 60/962,031, filed on Jul. 26, 2007. The subject matter of both International Application No. PCT/US2008/009012 and U.S. Provisional Application No. 60/962,031 is incorporated by reference as if fully set forth herein.

BACKGROUND OF THE INVENTION

The present invention relates to an apparatus capable of enabling a practitioner to thread a suture in a layer of subcutaneous tissue from a remote access point, to surgical methods facilitated by such an apparatus, and to associated tools useful with the apparatus for performing such surgical methods.

Various surgical methods, primarily in the field of plastic surgery, require the placement of a suture deep inside a layer of subcutaneous tissue from a remote access point. The typical procedure used is to first separate the layers of tissue (e.g., the facial tissue) for appropriate access, and to later suture the layers of tissue together, under tension. This, however, requires extensive surgery, which is expensive and which takes a significant amount of time (e.g., a matter of weeks) to heal.

Various procedures have been attempted to reduce the resulting trauma to a patient, the corresponding expense of the procedure, and the time required for recovery.

For example, one attempted procedure has been to implant a device having barbed profiles capable of engaging subcutaneous tissue at a location remote from the point of access. In practice, however, such barbs have been found to be prone to release after a relatively short period of time (on the order of a few months). Release of the barbs then allows the engaged tissue to sag.

Other attempted procedures have made use of suturing devices for facilitating placement of the suture from a remote access point. Such devices, however, are bulky mechanisms which, in practice, require considerable separation of the layers of tissue in order to reach the intended location, and are typically prone to the severing of blood vessels and nerves. Moreover, surgical procedures using such devices are complicated, and typically require the use of an endoscope, adding to the complexity of the desired procedure. Furthermore, such surgical procedures are highly invasive, time consuming and expensive, and require long recovery times.

As a consequence, there has long been a need in surgery, and in particular, facial plastic surgery, for a device which can be used to remotely place a suture and which can enter facial tissue with an incision of minimum size, so that scarring would not then ensue which could mar the resulting appearance. Further required is a surgical procedure that can provide a long term result by minimizing sagging due to migration of the sutures through tissue due to applied stresses, a problem which is commonly referred to in the art as a "cheese wire effect".

Various suturing instruments are well known in surgical practice, particularly those used in laparoscopic procedures in which the task is to sew together separated tissue, such as incisions made in skin or organs, by remote manipulation. For example, one such instrument is disclosed in U.S. Pat. No. 5,782,845, and includes a first elongated hollow body that can be passed fully through the tissue on one side of a wound or incision, and a second elongated body having an aperture which is passed fully through the other side of the wound or incision. The two bodies are brought together by an alignment device to achieve closure of the wound and to ensure that the ends of both bodies meet and coincide, employing what is essentially a lateral motion, for the passage of a suture.

However, because the internal side of the tissue typically contains a free medium such as air or a fluid, a suture threaded through the first body can pass through the aperture of the second body and can issue unimpeded into the internal side. Following this, the suture can be extracted by the second elongated body, having the aperture, and can be withdrawn to the exterior of the tissue, where it can be tensioned and knotted with the end of an opposing suture. Instruments of this type provide no spacings, within or between successive suture stitches.

Other suturing instruments are constructed much like hemostats, which employ a pincing motion that operates from a remote pivot, and are similarly suited for joining and attaching remote tissue.

A further consideration is that in practicing certain surgical procedures, particularly including facial plastic surgery, external manipulation is required from a remote access point, unlike wound closure, which requires local manipulation. The elongated hollow body of an instrument of the type disclosed in U.S. Pat. No. 5,782,845, must be guided by the apparatus for alignment with and for passing through a subcutaneous target aperture, and the guiding and docking motion to be employed must be virtually coincident with the axis of the hollow body. Otherwise, bunching of the tissue will occur, causing an unwanted cosmetic effect. For the example of a desired facial cosmetic surgical procedure, an appropriate alignment device must reference as close to the target aperture as is possible to prevent even slight looseness in the alignment mechanism from magnifying and causing misalignment between the hollow body and the aperture, thereby preventing penetration.

For cosmetic reasons, there is also a need to minimize the size of any apertures. Consequently, for facial cosmetic surgery, it is further necessary to use small diameter hollow bodies (preferably, 1.25 mm or smaller) to prevent the scarring of skin tissue. Moreover, to further prevent trauma, the surgical apparatus must be capable of storing the suture ends, for later extraction at a common external location on the face where the exposed ends are to be tensioned and tied together to complete the desired procedure.

A further consideration is that because suture material can buckle when subjected to axial compression, the hollow body must be capable of penetrating the aperture and the tissue by a sufficient distance to make room in the subcutaneous tissue for receiving the suture. Otherwise, the suture material will bunch up, and will fail to deploy to an adequate length for capture and extraction at the aperture. The apparatus could additionally be provided with an aperture which collapses with adequate force to clamp the suture ends during extraction.

Because the known devices were not capable of performing in this manner, it remained desirable to provide a surgical suturing apparatus which could overcome the fundamental deficiencies presented by such devices, to carry out a desired surgical procedure.

To this end, both U.S. Provisional Application No. 60/962,031 and International Application No. PCT/US2008/009012 disclosed various alternative embodiments of an apparatus which could place a suture deep inside a layer of subcutaneous tissue, from a remote access point, and which could be used to implement a surgical method for performing desired surgical procedures.

It has since been determined that other alternative embodiment devices can be developed for placing a suture deep inside a layer of subcutaneous tissue, from a remote access point, and for implementing surgical methods for performing desired surgical procedures, in addition to those disclosed in U.S. Provisional Application No. 60/962,031 and International Application No. PCT/US2008/009012.

SUMMARY OF THE INVENTION

In accordance with the present invention, alternative embodiment devices are provided which can place a suture deep inside a layer of subcutaneous tissue, from a remote access point, and which can be used to implement a surgical method for performing desired surgical procedures. Such apparatus and the corresponding surgical techniques are primarily intended for use in performing plastic surgery, and are particularly described in the context of performing a mid face lift. However, variations of the apparatus and method of the present invention are equally possible for use in performing neck lifts, brow lifts, under eye lifts, breast lifts, organ repositioning, and various other surgical procedures which similarly require the repositioning and the anchoring of tissues.

A tether insertion device is provided for delivering at least one tethering "strand" to the vicinity of the subcutaneous location where the surgical procedure is to be performed. In its preferred embodiment, the tether insertion device is generally comprised of a housing incorporating a nested pair of needles. The nested pair of needles includes an outer needle having a sharp tip and an inner needle having a blunt tip. The housing further includes an actuator for selectively advancing and retracting the outer needle relative to the inner needle. A spring return is preferably associated with the actuator and the housing so that the blunt tip of the inner needle is normally biased to project beyond the sharp tip of the outer needle.

In use, the exposed distal tip of the tether insertion device normally presents a blunt distal tip, to prevent unwanted trauma including nicking or severing of nerves or blood vessels. Upon advancement of the actuator, against the biasing forces of the spring, the sharp tip of the outer needle is caused to extend beyond the blunt tip of the inner needle, presenting a sharp tip useful for the desired penetration of tissues.

A suture insertion device is provided for positioning a tissue-supporting suture in a layer of subcutaneous tissue, for the formation of a subcutaneous sling having ends which can be used to implement a desired surgical procedure. In its preferred embodiment, the suture insertion device is generally comprised of a fixture incorporating alignment features for receiving one or more housings, each having an eyelet or an equivalent opening which can enter the tissue (for example, the facial skin) through established puncture points, combined with a guide associated with the fixture for establishing a passageway aligned with the eyelets (or openings).

The guide operates to receive a narrow gage needle, which functions as a cannula for passing a suture through the skin and subcutaneous tissue, and through the eyelets associated with the fixture, exiting the skin and coming to rest within an optional external guard. A suture can then be threaded through the needle so that, following removal of the needle, the suture passes through the skin and the subcutaneous tissue. Following this, steps are taken to form the suture into a subcutaneous sling having ends which can be anchored to provide support for accomplishing the desired surgical procedure.

To accomplish a desired surgical procedure, the tether insertion device is first preferably used to place one or more tethering stands in the vicinity of the subcutaneous location where the surgical procedure is to be performed. To this end, the actuator is used to advance the sharp tip of the outer needle beyond the blunt tip of the inner needle and the sharp tip of the outer needle is used to penetrate the skin in the vicinity of a desired, tissue-supporting anchoring point. Following this, the actuator is released, causing the sharp tip of the outer needle to retract beyond the blunt tip of the inner needle, presenting a blunt tip that can be used to pass the tethering strands through subcutaneous tissue.

As an example, and for the case of a mid face lift, the sharp tip of the outer needle is initially used to puncture the skin in the vicinity of the zygomatic arch, and to pierce the periosteum of the zygomatic arch. The blunt tip of the inner needle is then guided, by hand, through subcutaneous tissue, including the malar fat pad. The sharp tip of the outer needle is then used to exit the skin through exiting punctures located at a level slightly below the intended lift line. The tether insertion device is typically used twice, along different pathways, to deliver a pair of tethers for subsequent use in completing the desired procedure. The second tether is preferably caused to traverse the zygomatic arch, to facilitate use of the periosteum of the zygomatic arch as an anchoring point for the surgical procedure to be performed. The locations where the tethers are caused to pass through the skin are selected by the surgeon or other practitioner performing the procedure to achieve the desired amount of tissue engagement and the desired vector of the lift.

Following their insertion, the tethers are coupled with the eyelets of the housings, and the eyelets are then drawn upwardly, through the exiting punctures, to the intended lift line. The housings, together with the eyelets, are then assembled onto the frame of the suture insertion device, and the needle is advanced to traverse a passageway aligned with the eyelets. To this end, the needle is first caused to penetrate the skin, and to then follow a subcutaneous pathway through the eyelets. Following this, the needle is caused to exit the skin, preferably coming to rest inside the protective guard.

A suture is then passed through the needle, in turn passing though the skin, the subcutaneous tissue and the eyelets. The needle is then retracted and withdrawn, leaving the suture within the subcutaneous tissue, with ends projecting from the skin.

The fixture is then preferably retracted to withdraw the eyelets from the skin. Continued retraction of the fixture causes ends of the suture to exit from the skin, adjacent to the tethering strands. The tethers are then attached to the ends of the suture and the tethers, with the attached ends of the suture, are pulled through the punctures which received the eyelets, and through the subcutaneous tissue, eventually exiting through the puncture which was formed in the skin, above the zygomatic arch. This preferably establishes a generally triangular shaped sling having a horizontal portion at the established lift line, and an apex at the zygomatic arch. The suture is then tensioned, and tied off, producing the desired facial contour.

As an alternative, following placement of the suture, the eyelets can be detached from the housings. The tethering strands will then remain attached to the eyelets, which can be drawn upwardly, through the subcutaneous tissue, to eventually exit through the puncture which was formed in the skin, above the zygomatic arch. The suture, which is then engaged by the eyelets, will follow the eyelets through the subcutaneous tissue, eventually causing the ends of the suture to exit through the puncture which was formed in the skin, above the zygomatic arch. A triangular sling is again established, having a horizontal portion at the established lift line, and an apex at the zygomatic arch. The suture is then tensioned and tied off to produce the desired facial contour.

The foregoing enables what can be characterized as a "non-invasive" surgical procedure for repositioning and anchoring tissues, resulting from various improvements associated with the disclosed devices and methods employed, because no incision is required for performing the surgical procedure.

For example, both the tether insertion device and the suture insertion device employ short, thin (i.e., narrow gage) needles to reduce trauma and scarring of tissues. To this end, the relatively large diameter (e.g., 14 to 16 gage) cannulas which had previously been used for such procedures have been replaced with small diameter (e.g., 18 to 20 gage) needles, resulting in smaller punctures and eliminating the need for incisions, to minimize trauma and to eliminate the scarring of facial tissue.

Also contributing to this are both the nested needle structure of the tether insertion device, and the manner in which the eyelets of the suture insertion device are associated with the remainder of the apparatus. The nested needle structure minimizes trauma by providing a sharp tip for use when needed, but which otherwise presents a blunt tip for manipulation of the tether insertion device during the penetration of subcutaneous tissue, preventing the severing or nicking of nerves and blood vessels. The eyelets and their supporting subassemblies minimize trauma and prevent scarring by providing structures which can readily be attached to and separated from the remainder of the suture insertion device. This provides enhanced adaptability for accommodating the spacing variations of critical punctures that can be encountered during use, reducing the potential for trauma at the puncture points, and the scarring which could then result from such trauma.

In addition, use of the zygomatic arch as an anchoring point for a surgical procedure to be performed has been enhanced by improving the manner in which the periosteum is penetrated and engaged to form the desired anchoring point, avoiding the need to undermine surrounding tissues. To this end, a "rung" formation is developed in the periosteum, eliminating the need for the anchoring screws or staples that typically had been used to develop the required anchoring point.

Coupled with this is the development of a triangular shaped suture sling, and the provision of a temporary adjustment line for use when knotting the suture sling to the attachment point. The triangular shaped suture sling reduces the number of "corners" in the suture sling, in turn reducing the potential for causing unwanted dimples in subcutaneous tissue at the zygomatic arch, which can be seen on the surrounding skin. The temporary adjustment line allows the surgeon to externally manipulate the free ends of the suture sling during "tie off" of the subcutaneously located knot of the suture sling, eliminating excess tension, preventing the knot from unraveling and allowing the knot to be conveniently replaced with a fresh knot, if needed. This then gives the surgeon an improved ability to make final adjustments to the suture sling, or to completely replace the suture if needed.

The foregoing also eliminates the need for deep anesthesia, which had been associated with earlier procedures, minimizing recovery time and permitting such procedures to be performed in a physician's office with minimal assistance.

A further discussion of preferred apparatus for performing described surgical procedures is provided below, taken together with the following drawings.

BRIEF DESCRIPTION OF THE DRAWINGS

FIG. 7 is a partially sectioned, elevational view of the tether insertion device shown in FIG. 6, and which is configured to present a blunted tip.

FIG. 8 is a partially sectioned, elevational view of the tether insertion device shown in FIG. 6, and which is configured to present a sharpened tip.

FIG. 9 is a plan view of a first, alternative embodiment suture which can be used with the suture insertion device to perform a surgical procedure.

FIG. 10 is a plan view of a second, alternative embodiment suture which can be used with the suture insertion device to perform a surgical procedure.

DETAILED DESCRIPTION OF PREFERRED EMBODIMENTS

Figure 1:
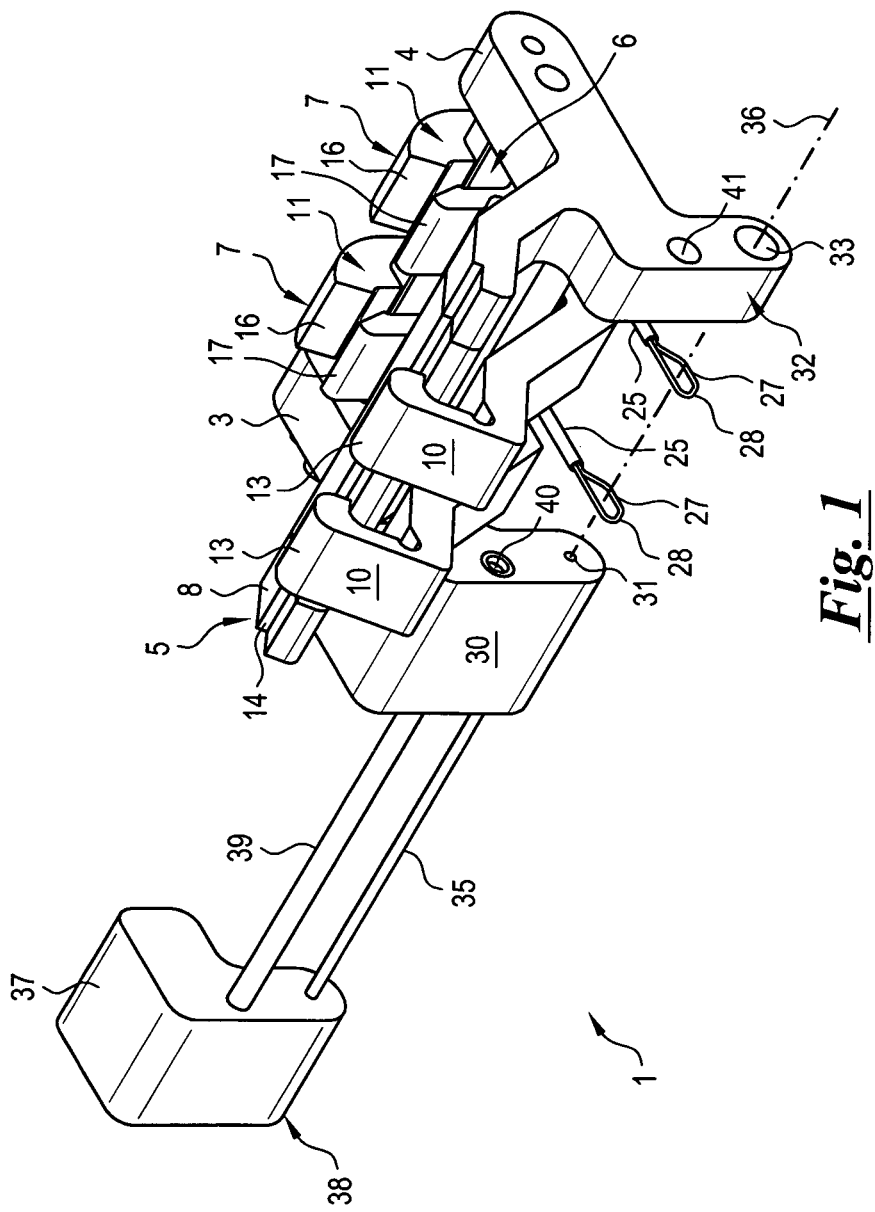
FIG. 1 is an isometric view of a suture insertion device produced in accordance with the present invention.

FIG. 1 shows a preferred device 1 for the insertion of a suture as will be described more fully below. As is further illustrated in FIG. 2, the device 1 generally includes a body 2 attached to and extending between a pair of arms 3, 4 associated with opposing ends of the body 2.

A first alignment member 5 projects from the body 2, and cooperates with the body 2 to provide the resulting fixture with suitable rigidity and structural support. The alignment member 5 preferably cooperates with a second alignment member 6 to form a slide for adjustably receiving one or more housings 7. In addition to receiving the housings 7, the second alignment member 6 also provides the fixture with additional rigidity and structural support.

In the preferred embodiment illustrated, the alignment member 5 terminates in a flange 8 which extends fully along the alignment member 5. The alignment member 6 preferably takes the form of a rod extending between the arms 3, 4, and which defines a longitudinal axis parallel to the body 2 and the flange 8. In the embodiment illustrated, two spaced and parallel rods are used to form the alignment member 6, to provide enhanced geometric orientation and structural support for the structures to be received by the alignment members 5, 6 of the body 2.

Figure 3:
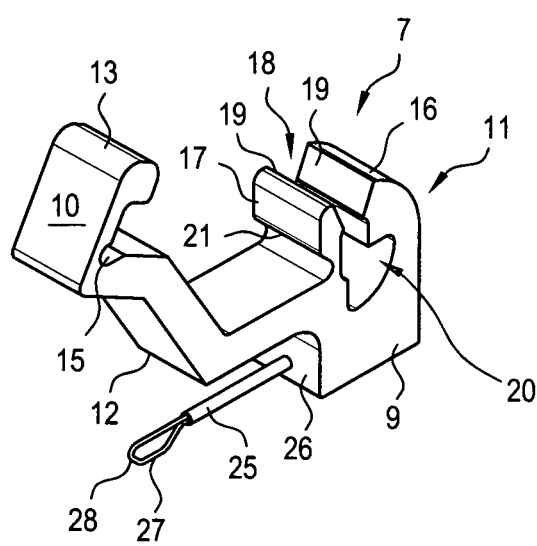
FIG. 3 is an isometric view of one of the housings shown in FIG. 1.

FIG. 3 illustrates a preferred embodiment housing 7 for cooperating with the alignment members 5, 6 of the body 2. The housing 7 includes a body 9 having a latch 10 for engaging the flange 8 of the first alignment member 5 and a catch 11 for engaging the rods of the second alignment member 6.

The latch 10 is connected to the body 9 of the housing 7 by an elbow structure 12 defining an extension and projecting at an angle which places the latch 10 in a position and in an orientation which is appropriate for engaging the flange 8 of the first alignment member 5. To this end, the latch 10 terminates in a catch 13 for cooperating with an undercut 14 formed in the flange 8, and includes an undercut 15 where the catch 13 meets the elbow structure 12 so the catch 13 can more easily flex in relation to the elbow structure 12.

The catch 11 extends from the body 9 of the housing to oppose the latch 10, and preferably includes an opposing pair of fingers 16, 17 for appropriately engaging the rods which form the second alignment member 6. To this end, the fingers 16, 17 are preferably spaced, at 18, to slidingly receive the rods forming the second alignment member 6, and each of the fingers 16, 17 preferably includes a sloping surface 19 for facilitating passage of the rods into a cavity 20 for receiving the rods forming the second alignment member 6 within the catch 11. The fingers 16, 17 can further include an undercut, such as the undercut 21 associated with the finger 16, so the finger can more easily flex in relation to the body 9 of the housing 7.

The cavity 20 is preferably arcuate in shape to facilitate engagement between the housing 7 and the alignment member 6. To this end, and referring to FIG. 4, the opposing fingers 16, 17 are first passed over the rods, facilitated by the sloping surfaces 19, so the rods can pass through the opening 18 and into the cavity 20. The arcuate shape of the cavity 20 then allows the housing 7 to be rotated through an angle on the order of 90 degrees, which in turn brings the catch 13 into engagement with the flange 8 of the alignment member 5. This then captures the rods between the fingers 16, 17 while the catch 13 is secured to the flange 8, mating the housing 7 with the alignment members 5, 6. As an alternative, the second alignment member 6 can be implemented with only a single rod, if desired, and the catch 11 can be formed with only one of the fingers 16 or 17.

The housing 7 is preferably adjustably mated with the alignment members 5, 6, for appropriate positioning as will be described more fully below. In the embodiment illustrated, when the rods of the alignment member 6 are passed between the fingers 16, 17 of the catch 11 and into the cavity 20, the housing 7 can slide along the alignment member 6 to appropriately position the housing 7 for the surgical procedure which is to be performed. Engagement of the housing 7 with the alignment members 5, 6 can then operate to secure the housing 7 in position responsive to frictional engagement between the housing 7 and the alignment members 5, 6. The housing 7 is preferably aligned and secured in position responsive to cooperation between the angled surfaces forming the elbow structure 12 of the housing 7 and the mating angled surfaces associated with the flange 8 of the alignment member 5 and the body 2, providing a self-aligning cooperation between the engaged structures. Repositioning of the housing 7 can be accomplished, if desired, by overcoming the frictional engagement developed between the housing 7 and the structures which receive it.

As an alternative, the housing 7 can be retained in a fixed position upon engagement with the alignment members 5, 6. This can include a fixed frictional engagement of the structures previously described, or engaging the housing 7 with aligning structures associated with the suture insertion device 1. This can also include fixed assembly of the housing 7 to the suture insertion device 1.

The housing 7 further includes an elongate member 25 extending from an end face 26 formed in the body 9 of the housing 7. The elongate member 25 can be solid or hollow, and preferably is implemented using an 18 to 20 gage needle, although other sizes can be used, if desired. The distal end of the elongate member 25 includes an eyelet 27. The eyelet 27 preferably includes a narrowed tip 28 to facilitate entrance of the eyelet 27, and the elongate member 25, into punctures formed in the skin that do not require an incision.

The eyelet 27 preferably has the shape of an elongated hole, but can have any of a variety of other shapes such as oval, circular, trapezoidal or rectangular, if desired. The maximum outer periphery of the eyelet 27, in transverse cross-section, is preferably no larger than the size of the punctures that will be formed in the skin to perform a desired surgical procedure, as will be described more fully below. The circumference of the elongate member 25 is also preferably no larger than the outer periphery of the eyelet 27, in transverse cross-section, so that when the elongate member 25 is to be inserted into the punctures for performing a desired surgical procedure, the eyelet 27 and the elongate member 25 will be appropriately sized when passing through the punctures formed in the skin.

The eyelet 27 can be made expandable and contractible, for example, using a shape-memory material similar to materials used to manufacture medical stents, to facilitate passage into the small punctures formed in the skin and to then expand into the desired shape after placement in subcutaneous tissue. As an alternative, an expandable eyelet of the type described in International Application No. PCT/US2008/009012 can be used. As a further alternative, the closed eyelet 27 can be replaced with an open eyelet, such as a hook extending from the tip of the elongate member 25, or can take the form of a probe (a web or a balloon) extending from the tip of the elongate member 25, which can be formed of a pierceable material.

Typically, the elongate member 25 will have a length on the order of 1 to 2 cm, although various other lengths can be employed. As an alternative, the length of the elongate member 25 can be made adjustable, to allow the elongate member 25 to penetrate inside subcutaneous tissue for various distances. As will be described more fully below, the elongate members 25 of a cooperating pair of housings 7, as is best shown in FIG. 1, will typically be spaced apart by approximately 1 cm, although other spacings can also be used. The selected spacing is made adjustable by the engagement developed between the housings 7 and the alignment members 5, 6 that receive them. The elongate members 25 shown in FIG. 1 project outwardly, substantially normal to the end faces 26 of the housings 7 which receive them. As an alternative, the elongate members 25 can project at an angle relative to the end faces 26 of the housings 7 which receive them, if desired, to accommodate a particular surgical procedure.

The elongate member 25 is straight in configuration. As an alternative, the elongate member, or other features of the suture insertion device 1, can be bent or contoured. Such variations can assist in entry into various sections of the face, such as beneath the eye or over the brow. For procedures beneath the eye, bent or contoured elongate members can be used to avoid contact with the eye, and for the case of a brow lift, bent or contoured structures can be used to follow the shape of the skull over the brow.

The elongate member 25 is preferably fixed to the body 9 of the housing 7, to prevent separation of the two structures during use of the suture insertion device 1, using an adhesive, a threaded engagement, or a friction fit. As an alternative, the elongate member 25 can be detachably connected to the body 9 of the housing 7, to facilitate separation of the two structures in appropriate cases, using a threaded engagement, a friction fit, a snap fit engagement or a releasable clamp. As an alternative, the eyelet 27 can similarly be detachably connected to the elongate member 25.

Figure 4:
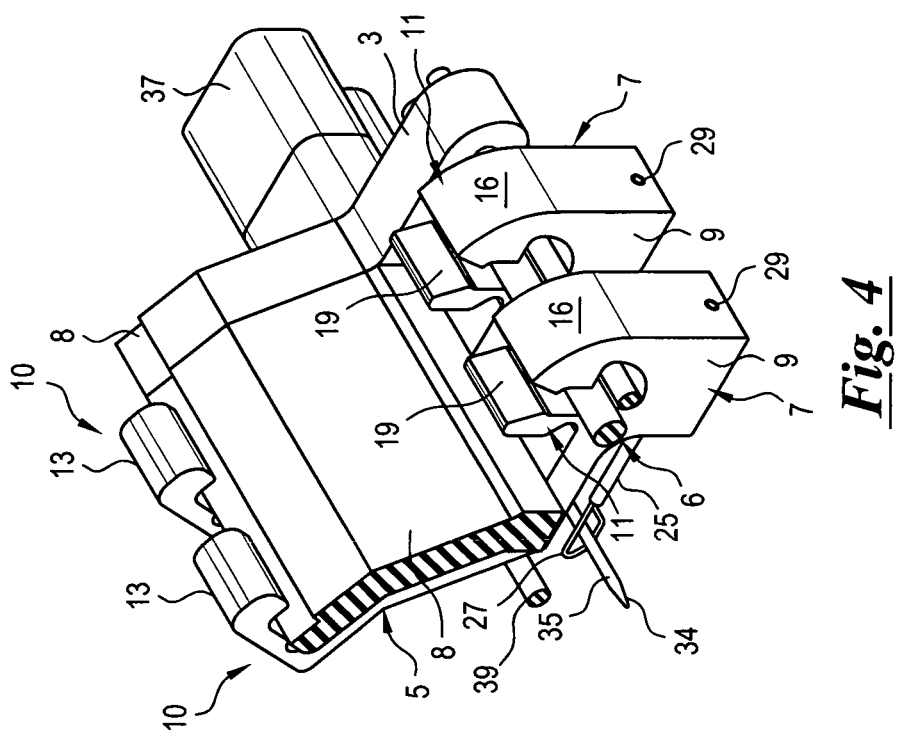
FIG. 4 is a partial isometric view, taken from the rear of the suture insertion device shown in FIG. 1.

As is best shown in FIG. 4, the body 9 of the housing 7 can be provided with an aperture 29 for communicating with the elongate member 25. For fixed connections between the elongate member 25 and the receiving housing 7, the aperture 29 can be used to pass structures for operating an expandable eyelet. For detachable connections between the elongate member 25 and the receiving housing 7, the aperture 29 can be used to pass structures for operating an expandable eyelet, or for engaging the elongate member 25 following detachment from the body 9 of the housing 7, for facilitating a surgical procedure as will be described more fully below, or for retrieving an elongate member 25 which has become embedded in the subcutaneous tissue. As an alternative, the elongate member 25 can pass through and project from the aperture 29 in the body 9 of the housing 7, as is shown in FIG. 3.

Figure 2:
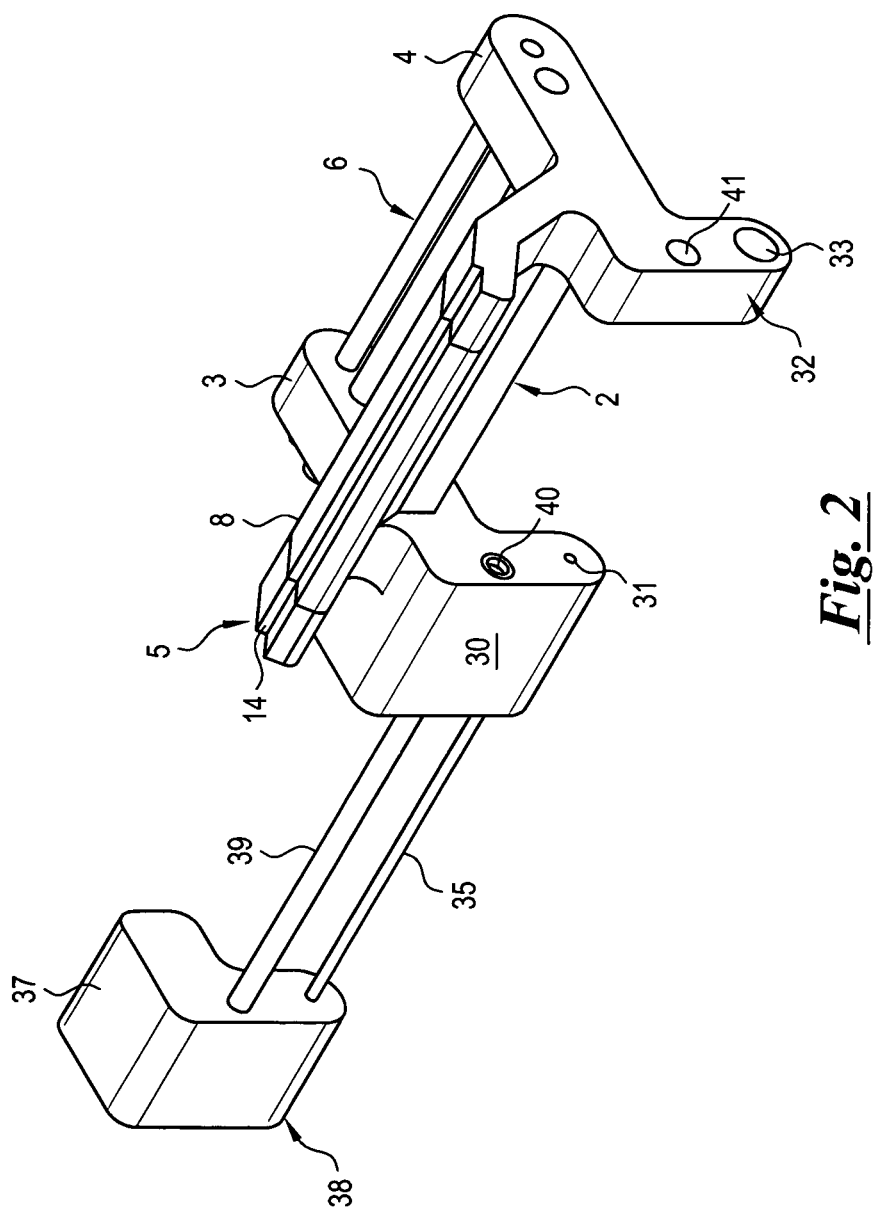
FIG. 2 is an isometric view of the suture insertion device shown in FIG. 1, with the housings removed.

As is further illustrated in FIGS. 1 and 2, the arm 3 is provided with a guide 30 depending from the arm 3 and which is oriented substantially perpendicular to the longitudinal axis of the arm 3. The guide 30 includes an aperture 31 which serves as a keying structure for receiving a suture-feeding structure so the suture-feeding structure will be oriented into alignment with the eyelets 27. Bottom surface portions of the guide 30 can also serve to depress adjacent tissue to facilitate the entrance of the suture-feeding structure into subcutaneous tissue, as will be described more fully below.

As is further shown in FIGS. 1 and 2, the arm 4 is provided with a guard 32 depending from the arm 4 and which is oriented substantially perpendicular to the longitudinal axis of the arm 4. The guard 32 defines an open region 33 for receiving the end of the suture-feeding structure, as will be described more fully below, primarily for purposes of receiving the end of the suture-feeding structure in a manner that helps prevent prick injury of the user of the fixture. The illustrated open region 33 is generally cylindrical in shape. As alternatives, the open region 33 can have other shapes, including partial closures such as "C" shaped regions, if desired, for providing better access and visibility of the tip 34 of the needle 35. The guard 32 also serves to depress tissue, to facilitate the exit of the suture-feeding structure from subcutaneous tissue, as will be described more fully below. As an alternative to the guard 32, a spatula or some other equivalent structure can be used to depress the tissue.

The guide 30 and the aperture 31 operate to direct a suitable suture-feeding structure, such as the illustrated needle 35, or some other equivalent shaft, along a centerline 36 which extends through the guide 30, through the eyelets 27 of the elongate members 25 of the housings 7 associated with the body 2 of the fixture, and into the guard 32, which are each aligned with the centerline 36. Opposing faces of the open region 33 of the guard 33 are preferably located within a few millimeters of the centerline 36. Such structures operate to control the traverse of the needle 35 through the subcutaneous tissue following desired penetration of the skin, to be more fully described below, enabling the needle 35 to penetrate the eyelets 27 following penetration of the skin, and to exit the skin and enter the protective, open region 33 of the guard 32. To this end, the distal end 34 of the needle 35 includes a sharpened tip capable of penetrating tissue. As an alternative, other structures, examples including hinged or pivoting structures, can similarly be used to guide a suitable suture-feeding structure along a desired (e.g., straight or curved) path.

Movement of the needle 35 within the guide 30 and along the centerline 36 is preferably controlled using an actuator 37 fixed to a proximal end 38 of the needle 35, which is readily grasped by the user of the device 1. To provide the narrow gage needle 35 with additional structural support, a support rod 39 is also preferably coupled with the actuator 37 and is received in an additional aperture 40 formed in the guide 30 to maintain the alignment of the needle 35 during advancement and retraction of the needle 35 responsive to movements of the actuator 37. The guard 32 is preferably provided with an additional open region, at 41, for receiving the end of the support rod 39. More than one support rod can be associated with the actuator 37 and the guide 30, if desired, or some other suitably shaped shaft, beam or keyed structure can be used to provide additional support for the narrow gage needle 35.

The sharpened tip 34 of the needle 35 is preferably ground at a slanted angle, and the slanted tip 34 is preferably offset and radially oriented in accordance with the shape of the eyelet 27 to facilitate entry of the tip 34 into the eyelet 27. The rod 39 is coupled with the needle 35, through the actuator 37, and assists in maintaining the rotational orientation of the offset tip 34.

The proximal end 38 of the needle 35 is configured to receive a suture, as will be described more fully below. To this end, the actuator 37 preferably includes a taper at the point of entry to the proximal end 38 of the needle 35 to facilitate the insertion of a suture into and through the needle 35.

As an alternative, a conventional cannula can be used to provide the functionality of the needle 35, in place of the actuator 37 and the support rod 39. In such case, the cannula preferably includes a hub to provide a smooth tapered entrance along the inside diameter of the cannula, to allow the suture to be smoothly threaded into the cannula, or a hubless cannula can be used, if preferred.

As a further alternative, the suture can be coupled with outer portions of the needle 35. For example, the suture can be attached to the periphery of the needle 35, preferably near the tip 34, or the tip 34 of the needle 35 can be provided with an aperture for engaging the suture. In such cases, the needle 35 can be hollow, or solid if preferred. Advancement of the actuator 37 can then pull the suture through the suture insertion device 1, without requiring the suture to be threaded through the needle 35.

The exposed length of the needle 35, from the actuator 37 to the distal tip 34, is set so that the sharp tip 34 does not protrude beyond the guard 32 when the needle 35 is fully inserted into the aperture 31 of the guide 30 and through the eyelets 27, and the actuator 37 is thrust to a forward-most position against the guide 30, to provide the needle 35 with a length appropriate for ensuring that the sharp tip 34 rests within the guard 32. The exposed length of the rod 39 is similarly set to that the distal tip of the rod 39 does not protrude beyond the guard 32 when the actuator 37 is thrust to a forward-most position against the guide 30, to provide the rod 39 with a length appropriate for ensuring that the tip of the rod 39 rests within the open region 41. The dimensions of the aperture 31 and the eyelets 27 are preferably selected to accommodate a sharpened, narrow gage needle, as previously indicated. However, other dimensions can be employed to accommodate different needle sizes, if preferred.

As previously indicated, the needle 35 and the rod (or rods) 39, if used, are moved axially along the centerline 36 for advancement and retraction of the needle 35 through the skin and subcutaneous tissue. Suitable structures, for example, a spring operated detent, can be provided in the guide 30 for interacting with a cooperating structure formed in the rod 39, or the needle 35, to latch the needle 35 in a desired position relative to the guide 30 (e.g., a fully advanced position, a fully retracted position, or some intermediate position for facilitating the surgical procedure to be performed), or to prevent separation of the needle 35 from the guide 30 (e.g., to prevent potential prick injury, or to facilitate a subsequent re-insertion of the needle 35 to perform a desired surgical procedure).

To be noted is that the device 1 shown in FIGS. 1 to 4 is designed for use on the left side of the face of a patient. As an alternative, and to function on the right side of the face of a patient, a mirror image version of the device 1 can be used to reverse the locations of the various structures illustrated.

Figure 5:
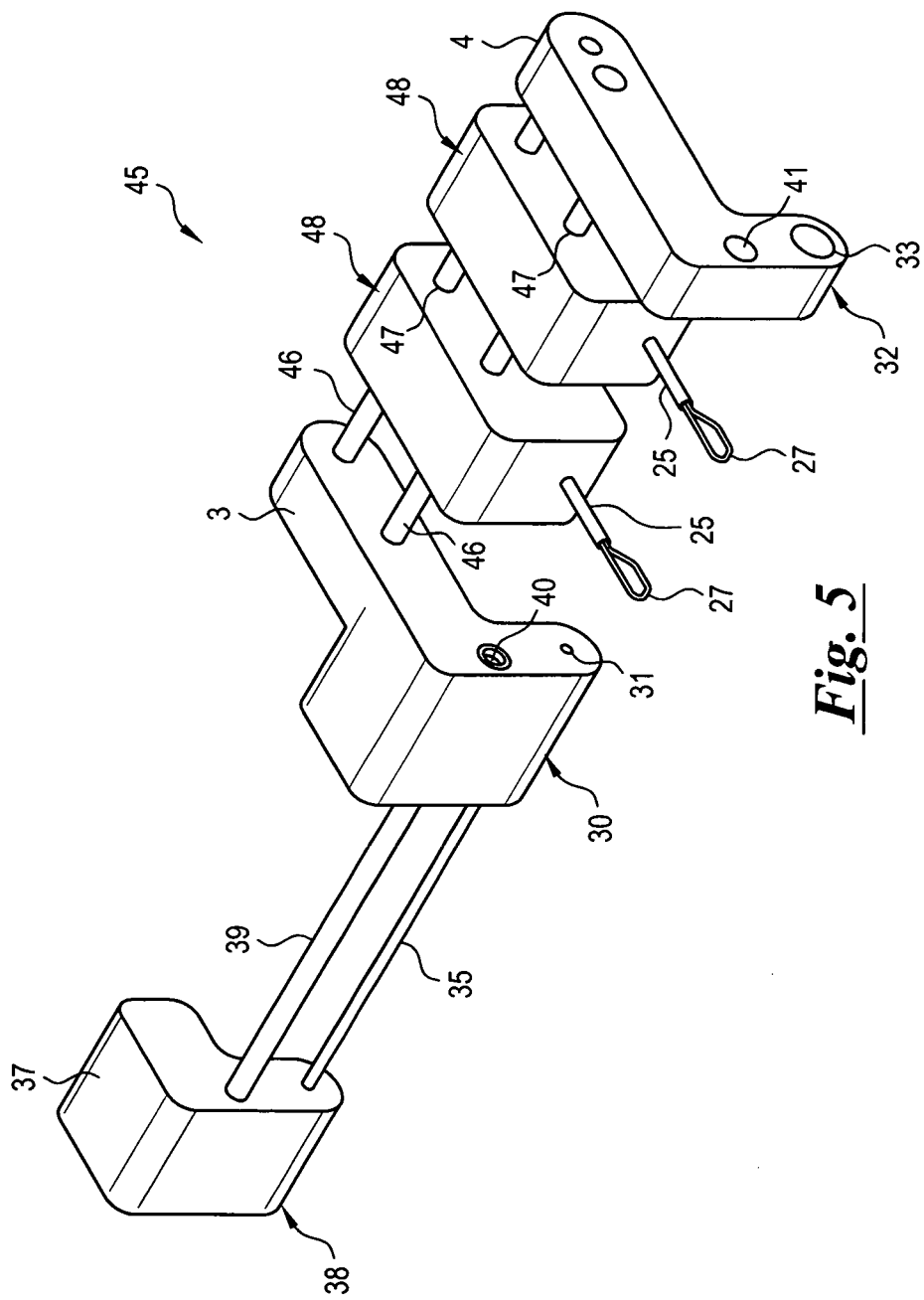
FIG. 5 is an isometric view of an alternative embodiment of a suture insertion device produced in accordance with the present invention.

FIG. 5 shows an alternative embodiment of the suture insertion device 1 shown in FIGS. 1 to 4. The configuration of the suture insertion device 45 shown in FIG. 5 has various features in common with the suture insertion device 1 shown in FIGS. 1 to 4, but exhibits some variations. In the description which follows, components corresponding to those previously described have corresponding reference numbers.

The alternative embodiment suture insertion device 45 shown in FIG. 5 replaces the first alignment member 5 and the second alignment member 6 with a spaced pair of rods 46 extending between the arms 3, 4. The rods 46 separate the arms 3, 4, as previously described, and engage bores 47 formed in a pair of housings 48 so the housings 48 can slide along the rods 46. The housings 48 each include an elongate member 25 with an eyelet 27 corresponding to the elongate members 25 and the eyelets 27 of the housings 7 of the suture insertion device 1 shown in FIGS. 1 to 4. The housings 48 can either be preassembled with the remainder of the suture insertion device 45, or one or more of the arms 3, 4 can be made detachable from the rods 46 using a suitable detachable connection such as a threaded arrangement, a friction fit or a snap fit engagement, to allow the housings 48 to be assembled and disassembled during use of the suture insertion device 45.

As a further alternative, the arms 3, 4 shown in FIGS. 1 to 4 are permanently connected to the body 2 of the suture insertion device 1. It is also possible for the arms 3, 4 to be releasably connected to the body 2 of the suture insertion device 1, for example, using threaded fasteners. This then allows the suture insertion device 1 to be assembled during a surgical procedure, if desired. This also allows the suture insertion device 1 to function on the opposing side of the face of a patient, without requiring the use of a separately configured version of the device, by allowing the arms 3, 4 to suitably be switching from side to side to reverse the locations of the various structures illustrated.

Figure 6:
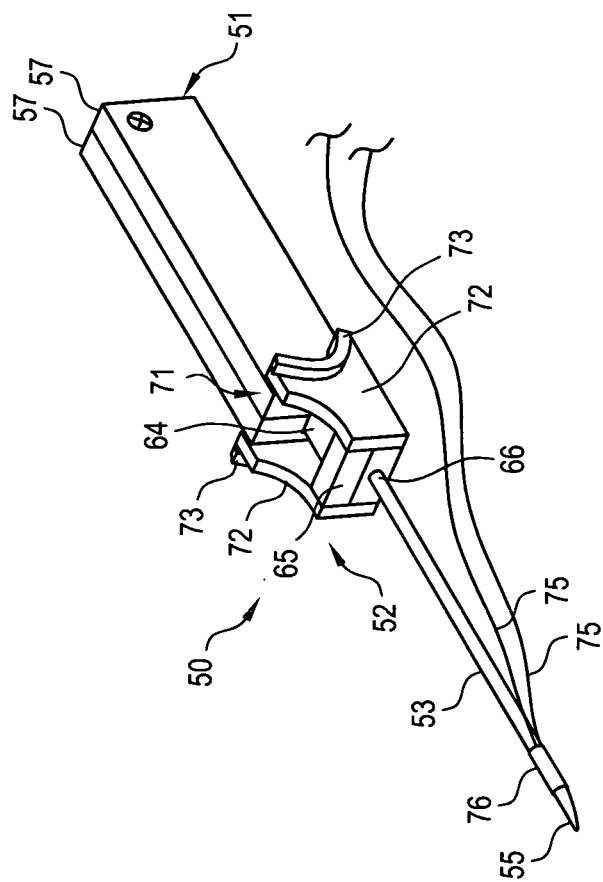
FIG. 6 is an isometric view of a tether insertion device produced in accordance with the present invention, and which is configured to present a sharpened tip.

FIGS. 6 to 8 show a preferred device 50 for the insertion of a tether, or plural tethers, which can be used to position a suture for performing a desired surgical procedure as will be described more fully below. The device 50 generally includes a housing 51, an actuator 52 coupled with the housing 51, and a nested pair of needles 53, 54. An outer needle 53 is coupled with the actuator 52 and includes a sharpened tip 55. An inner needle 54 is coupled with the housing 51 and includes a blunted tip 56. The outer needle 53 has a diameter which is sized slightly larger than the diameter of the inner needle 54, allowing the outer needle 53 to slide relative to the inner needle 54.

The combined outer needle 53 and inner needle 54 will typically have lengths on the order of 2 to 4 inches, although various other lengths can be employed. The outer needle 53 is preferably implemented using an 18 to 20 gage needle, although other sizes can be used, if desired. The inner needle 54 can be implemented as a hollow structure, but is preferable formed as a solid rod. The inner needle 54 will have a diameter which is appropriate for allowing the outer needle 53 to freely slide relative to the inner needle 54 during use of the tether placement device 50 as will be described more fully below.

As is best shown in FIG. 6, the housing 51 is formed of a pair of split segments 57 connected using suitable fasteners such as the screws shown in FIG. 6. Referring to FIGS. 7 and 8, the split segments 57 of the housing 51 cooperate to define a series of structure-receiving cavities.

A cavity 58 is provided for receiving the nested pair of needles 53, 54. The inner needle 54 extends longitudinally through the cavity 58, to a notch 59 in the rear face 60 of the housing 51. The proximal end 61 of the inner needle 54 can be frictionally retained within the notch 59, between the split segments 57, or an adhesive can be used to fix the end of the inner needle 54 in the notch 59. This develops an annular space 62 between the inner needle 54 and the split segments 57 which is suitable for slidingly receiving the outer needle 53 responsive to operation of the actuator 52.

A cavity 63 is provided for receiving a slide 64 associated with the actuator 52. As is best shown in FIG. 6, the slide 64 is coupled with the body 65 of the actuator 52. The proximal end 66 of the outer needle 53 is received in the body 65, and can be frictionally retained within the body 65, or an adhesive can be used to fix the needle 53 within the body 65. The outer needle 53 is then free to slide relative to the fixed inner needle 54, responsive to movements of the actuator 52, within the annular space 62 developed in the cavity 58.

A cavity 67 is provided for receiving a spring 68 which extends between a pawl 69 associated with the rear end 70 of the slide 64 and the front face 71 of the housing 51. As a result, the actuator 52 is normally biased toward a retracted position, under the influence of the spring 68, which draws the actuator 52 toward the housing 51.

The lengths of the outer needle 53 and the inner needle 54 are selected so that when the actuator 52 is in the retracted position (as is shown in FIG. 7), the blunted distal tip 56 of the inner needle 54 projects beyond the sharpened distal tip 55 of the outer needle 53. This presents a blunted leading edge upon advancement of the tether insertion device 50 into tissue.

Side faces 72 of the actuator 52 extending from the body 65 are provided with contoured finger engagement grips 73. The grips 73 allow a user to advance the actuator 52 against the biasing forces of the spring 68 (as is shown in FIGS. 6 and 8), causing the sharpened distal tip 55 of the outer needle 53 to project beyond the blunted distal tip 56 of the inner needle 54. This presents a sharp leading edge upon advancement of the tether insertion device 50 into tissue.

In use, one or more tethers 75 are attached to the outer needle 53, toward the distal end 55. The tethers 75 can be attached to the needle 53 using a sheath 76 formed of a heat shrinkable material for engaging the tethers 75, by gluing the tethers to the outer needle 53, or using some other appropriate attachment method. Materials such as 4-0 suture material are presently considered preferred for use in forming the tethers. Other equivalent materials could also be used, if desired. The tethers can be straight lengths, or can be looped at their distal ends (folded or pre-formed), as preferred.

The device 50 shown in FIGS. 6 to 8 is designed for use on either the left side or the right side of the face of a patient.

Modifications of the device 50 may be required for other surgical procedures performed on other portions of the body, including changes in the lengths of the needles 53, 54 and/or needles that are curved or contoured.

The various structures associated with the suture insertion devices 1, 45 and the tether insertion device 50 can be formed of any of a variety of materials that offer a sterile field, including various plastics and metals.

Examples of various surgical procedures which can be performed using the above-described devices are given in the description which follows. Although the following description is primarily directed to surgical procedures for performing a mid face lift, and while other lifting procedures will be more briefly described, including neck lifts and forehead lifts, it is to be understood that any of a variety of different surgical procedures can similarly be performed, and that the steps employed in performing such procedures can freely be varied responsive to the requirements and preferences of the surgeon or other practitioner performing a particular procedure.

Any of a variety of conventional sutures can be used to perform the surgical procedures being described, including natural, synthetic and metallic suture materials of appropriate diameter and length. As an alternative, sutures having various anchors or other tissue-engaging features can be used to facilitate suture placement.

FIG. 9 shows a tissue-engaging suture 80 which includes sections 81, 82 formed of an otherwise conventional suture material, separated by a modified portion 83. In the configuration shown, the modified portion 83 is implemented as a thickened section which is preferably centrally located between the sections 81, 82. Additional modified portions 83, separating additional sections of otherwise conventional suture material, can also be provided if indicated. It has been found that, in practice, such a suture construction can distribute stress better than a conventional suture. Such a suture construction also enhances retention of the suture in position, and further prevents the well known problem caused when conventional sutures improperly migrate through tissue (i.e., so-called "cheese wire effect").

As an example, the thickened portion can have a length of approximately 1 cm, and a thickness on the order of 1 mm. Various techniques can be used to provide the suture 80 with a thickened section, including knotting, braiding, weaving, molding, the affixing of a sleeve, beading, coiling, kinking, etc. Many of these techniques can be used to develop absorbent regions, and crevices capable of providing beneficial cavities into which tissue growth can penetrate, in turn providing additional bonding.

FIG. 10 shows another tissue-engaging suture 85. The suture 85 includes a pair of modified portions 83 which are separated by a center section 86 formed of an otherwise conventional suture material. The center section 86 is further preferably provided with a marker 87, or with one or more knots positioned at 87, to facilitate alignment of the suture 85 when in use. For the suture embodiments shown in FIGS. 9 and 10, the thickened sections 83 should have a sufficient diameter to prevent passage of the suture 80, 85 up the penetrating channels that are developed during the surgical procedure being performed.

It is to be understood that the sutures 80, 85 are provided for purposes of facilitating the procedures to be described below, but that use of these sutures is optional. Conventional surgical sutures, as well as conventional surgical instruments, can also be used, if preferred, and the various sutures and instruments can either be used in the manner described below, or in conjunction with other procedures described herein or developed by the skilled practitioner.

An example of a surgical procedure will now be described which can be practiced to perform a mid face lift. It is to be understood that while the steps to be described are presently considered preferred, such procedures can be varied responsive to the requirements of a given procedure, and the preferences of the surgeon or other practitioner performing such procedure. Such steps can similarly be used to perform other surgical procedures either using the steps which will be described below, or suitable variations of such steps, such as variations in the method of entry and anchoring.

The initial steps of the overall procedure are preferably performed to establish an anchor which will later be used to secure a tissue-lifting suture (or "sling"). As an alternative, establishment of the anchor can be postponed until after placement of the suture sling. In either case, the location of the anchor for a mid face lift is preferably in the zygomatic arch of the upper face.

Figure 11:
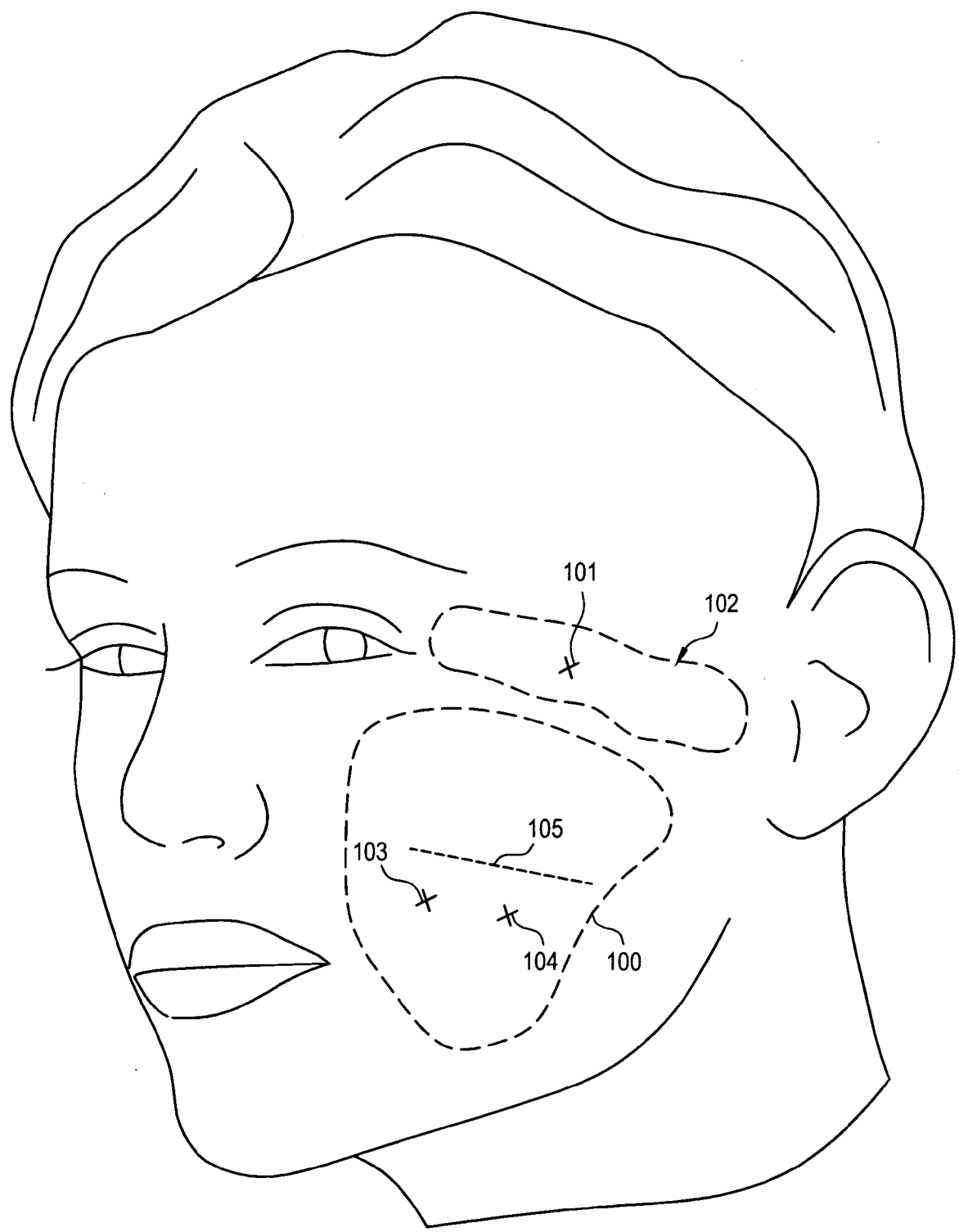
FIGS. 11 through 16 are sequential illustrations providing an example of one of the surgical procedures which can be performed in accordance with the present invention using the tether insertion device.

Referring to FIG. 11, the boundary of the malar fat pad, shown at 100, identifies the region where a mid face lift is to be conducted. A mark 101 is placed where a typical skin accessing puncture is to be located, over the zygomatic arch 102. Marks 103, 104 are placed to identify locations where additional skin accessing punctures are to be located. For a typical mid face lift, the marks 103, 104 are preferably set to establish a 1 cm spacing between the accessing punctures. A transverse line 105 corresponding to the centerline 36 developed by the suture insertion device 1 indicates where support for the lift is to be established. The spacing developed between the locations 103, 104 corresponds to a typical length to be established for the base of a sling for supporting tissue, as will be described more fully below. As an example, and for the procedure which has been selected for illustration in the drawings, the tissue-supporting sling is substantially triangular in shape. Tissue-supporting slings having other shapes can also be developed, for the mid face lift which has been selected for illustration, or for other surgical procedures to be performed. These various locations can be marked using conventional methods, or using marking devices of the type described in U.S. Provisional Application No. 60/962,031 and International Application No. PCT/US2008/009012.

Figure 12:
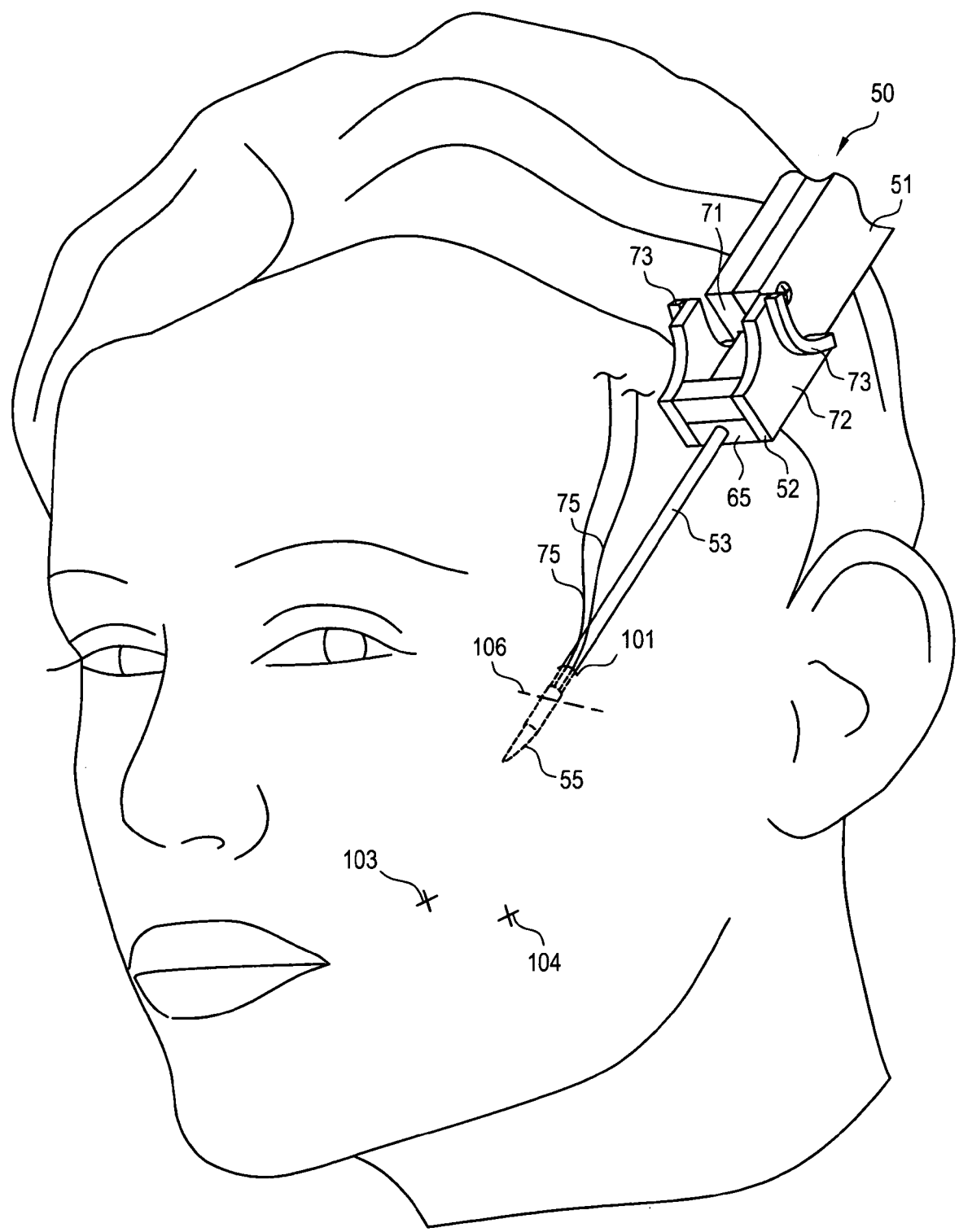

Referring next to FIG. 12, the tether insertion device 50 shown in FIGS. 6 to 8 is first used to install two tethers 110, 111 that will later be used to facilitate the lift procedure to be performed. To this end, the housing 51 of the tether insertion device 50 is grasped by the user while engaging the grips 73 of the actuator 52, allowing the user to advance the actuator 52 against the biasing forces of the spring 68 to cause the sharpened distal tip 55 of the outer needle 53 to project beyond the blunted distal tip 56 of the inner needle 54. This then presents a sharp leading edge upon further advancement of the tether insertion device 50, for puncturing the entry point 101. Further advancement of the tether insertion device 50 then causes this sharp leading edge to puncture the periosteum, shown at 106, which covers the bone beneath the zygomatic arch 102, for purposes of establishing a "rung" of strong tissue that can later be used to anchor a tissue-supporting sling. As an alternative, the rung can be established using the ligament of the zygomatic arch.

Figure 13:
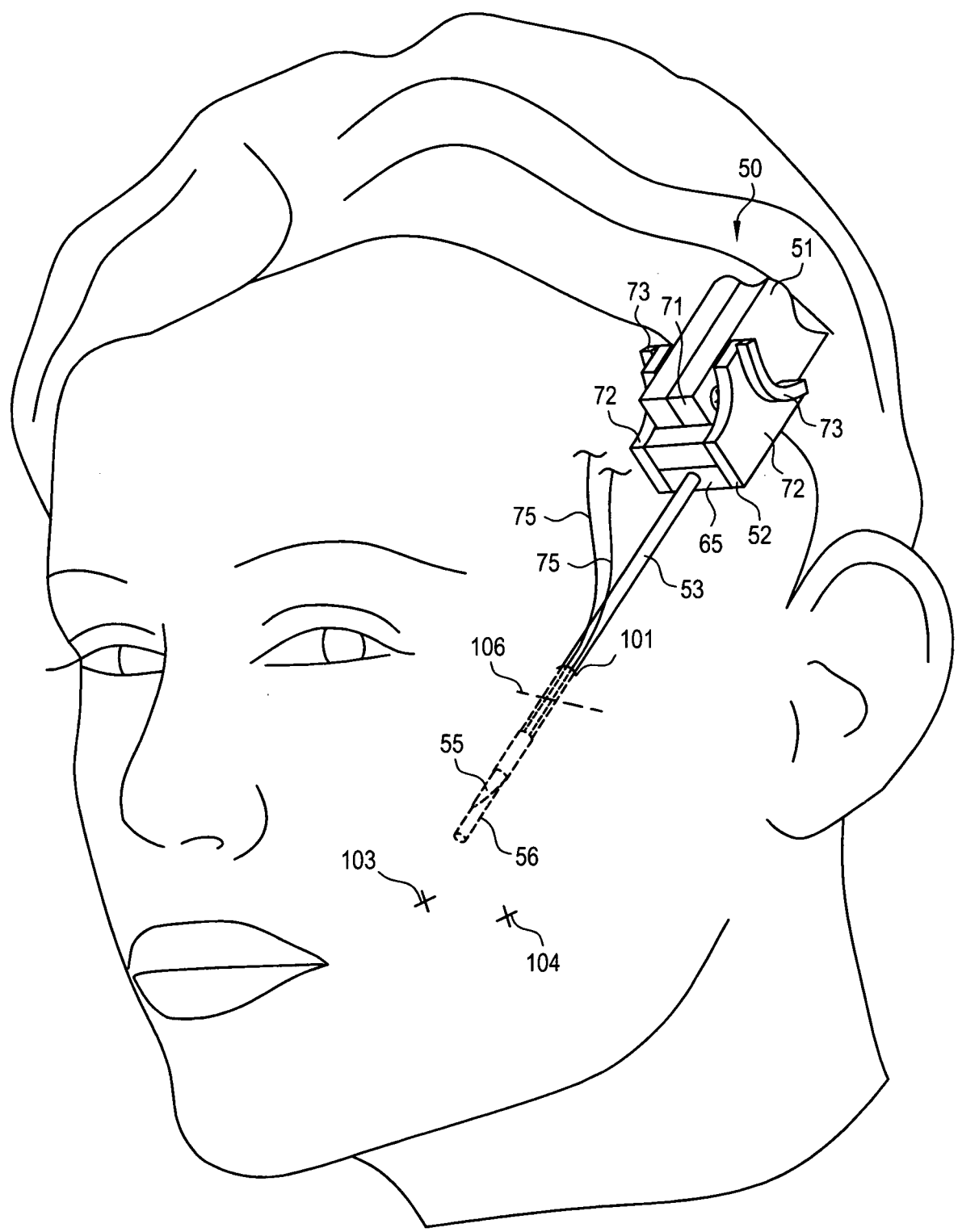

Referring next to FIG. 13, and after the periosteum has been punctured, the grips 73 are preferably released, which causes the actuator 52 to retract responsive to the spring 68. This then causes the blunted distal tip 56 of the inner needle 54 to project beyond the sharpened distal tip 55 of the outer needle 53, presenting a blunted leading edge for continued subcutaneous advancement of the tether insertion device 50 without the risks of trauma to nerves and blood vessels that would otherwise be associated with a sharp leading edge.

The tether insertion device 50 is then guided, by hand, toward the exit mark 103. The plan angle of this first insertion will correspond to a first vector in the direction of the exit mark 103. The grips 73 of the actuator 52 are then used to extend the sharpened distal tip 55 of the outer needle 53 beyond the blunted distal tip 56 of the inner needle 54, presenting a sharpened leading edge for puncturing and passing through the exit mark 103, as shown in FIG. 14.

To perform a particular surgical procedure, or to meet user preferences, situations may arise where the presentation of a sharp tip is preferred for use in placement of the tethers 110, 111. In such cases, the grips 73 of the actuator 52 can be used to maintain the sharpened distal tip 55 of the outer needle 53 in a position which extends beyond the blunted distal tip 56 of the inner needle 54, or the structures associated with the needles 53, 54 can be modified to normally bias the sharpened distal tip 55 of the outer needle 53 to project beyond the blunted distal tip 56 of the inner needle 54. As a further alternative in such cases, a standard needle having a sharpened tip can be used in place of the tether insertion device 50. The tethers 110, 111 can be attached to a hollow or a solid needle using one of the techniques which were used to attach the tethers 75 to the needle 53 of the tether insertion device 50, or by engaging the tethers 110, 111 in an aperture formed in the tip of the standard needle. As an alternative, the tethers 110, 111 can be threaded through a hollow standard needle, either before insertion of the needle, to project beyond the tip so the tethers 110, 111 can then be pulled through desired tissues responsive to advancement of the standard needle, or after insertion of the needle, so the tethers 110, 111 can then be threaded through the hollow needle, and the desired tissues.

Figure 14:
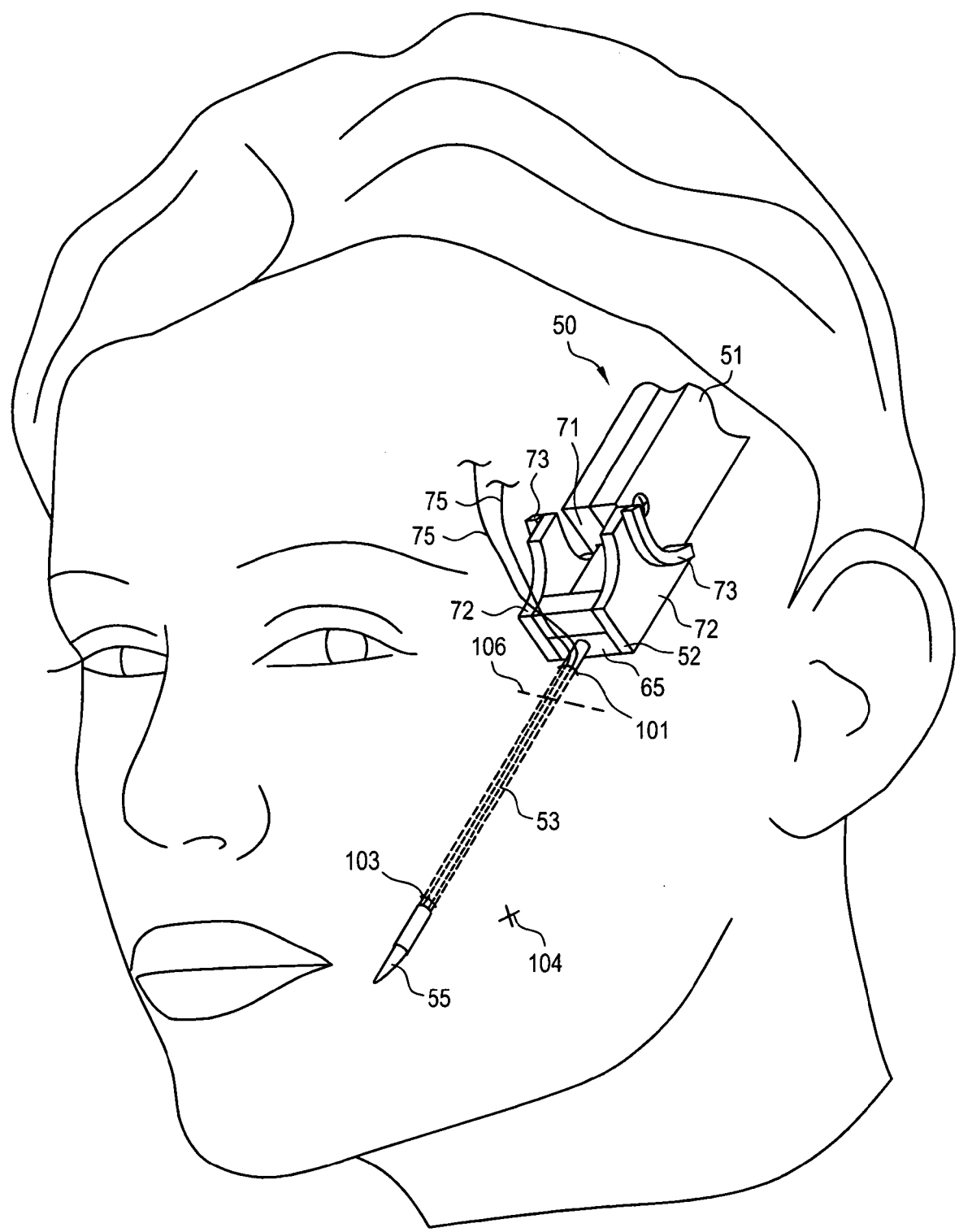

Referring next to FIG. 14, the leading edge of the tether insertion device 50 will extend from the exit puncture 103, exposing ends 114, 115 of the tethers 110, 111. The end 114 of the tether 110 is then separated (pulled or cut) from the outer needle 53. Following this, the tether insertion device 50 is withdrawn while the end 114 of the tether 110 is grasped, causing the tether 110 to remain extended from the exit puncture 103 while the leading edge of the tether insertion device 50 is retracted toward the entry puncture 101, as shown in FIG. 15.

Figure 15:
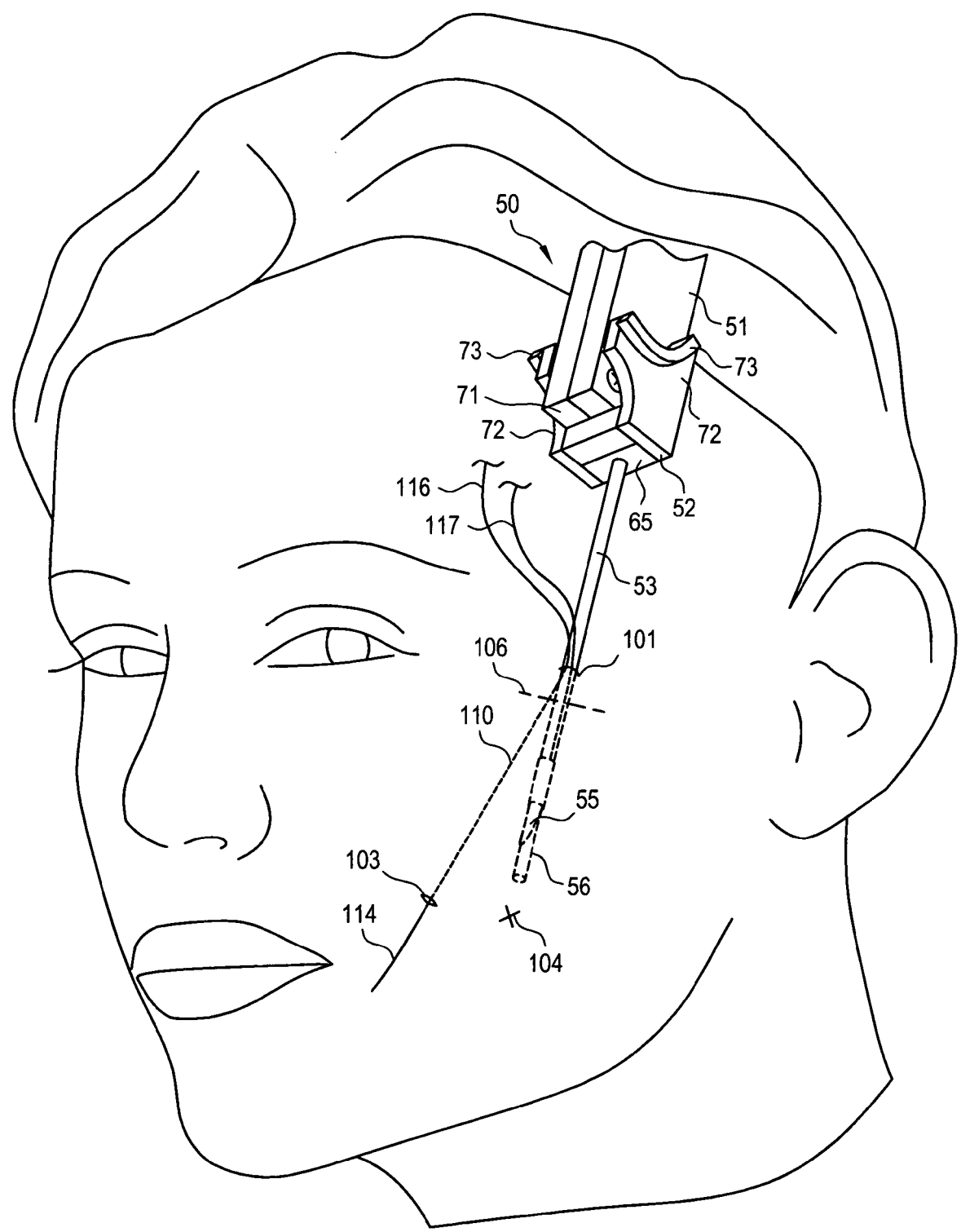

Referring next to FIG. 15, the leading edge of the tether insertion device 50 is retracted beyond the periosteum 106 while the tether 110 remains in place within the exit puncture 103, the periosteum 106, and the entry puncture 101, forming a first subcutaneous pathway through the malar fat pad 100. The tether insertion device 50 is then repositioned, by hand, and directed toward the exit mark 104 for the insertion of a second tether. The plan angle of this second insertion will correspond to a second vector. A second vector which is approximately 15 degrees from the first vector is presently considered preferred, to establish a preferred separation between the exit punctures 103, 104 of approximately 1 cm. Portions of the pathway defined by the second vector can correspond to portions of the pathway defined by the first vector, provided that appropriate separation is maintained between the exit punctures 103, 104.

The leading edge of the tether insertion device 50 preferably remains beneath the skin, inside the entry puncture 101, during the repositioning of the tether insertion device 50 to prevent withdrawal of the leading edges of the nested needles 53, 54 from the skin during insertion of the second tether. This then avoids the need to re-enter the puncture 101 to make this second pass, to once again minimize trauma to the entry puncture 101 and to minimize the occlusion of tissues between the pathway for the second tether and the entrance to the periosteum (or to other anchoring tissues or structures). The leading edge of the tether insertion device 50 also preferably remains blunted during retraction to the periosteum 106 and during advancement to the second exit point 104, to avoid the risk of trauma to nerves and blood vessels that would otherwise be associated with a sharp leading edge.

The grips 73 of the actuator 52 are then used to extend the sharpened distal tip 55 of the outer needle 53 beyond the blunted distal tip 56 of the inner needle 54, presenting a sharpened leading edge for puncturing and passing through the exit mark 104, so that the leading edge of the tether insertion device 50 will then extend from the exit puncture 104, exposing an end 115 of the tether 111. The end 115 of the tether 111 is then separated (cut or pulled) from the outer needle 53. Following this, the tether insertion device 50 is withdrawn while the end 115 of the tether 111 is grasped, causing the tether 111 to remain extended from the exit puncture 104, as is shown in FIG. 16, while the tether insertion device 50 is retracted toward and removed from the entry puncture 101.

Figure 16:
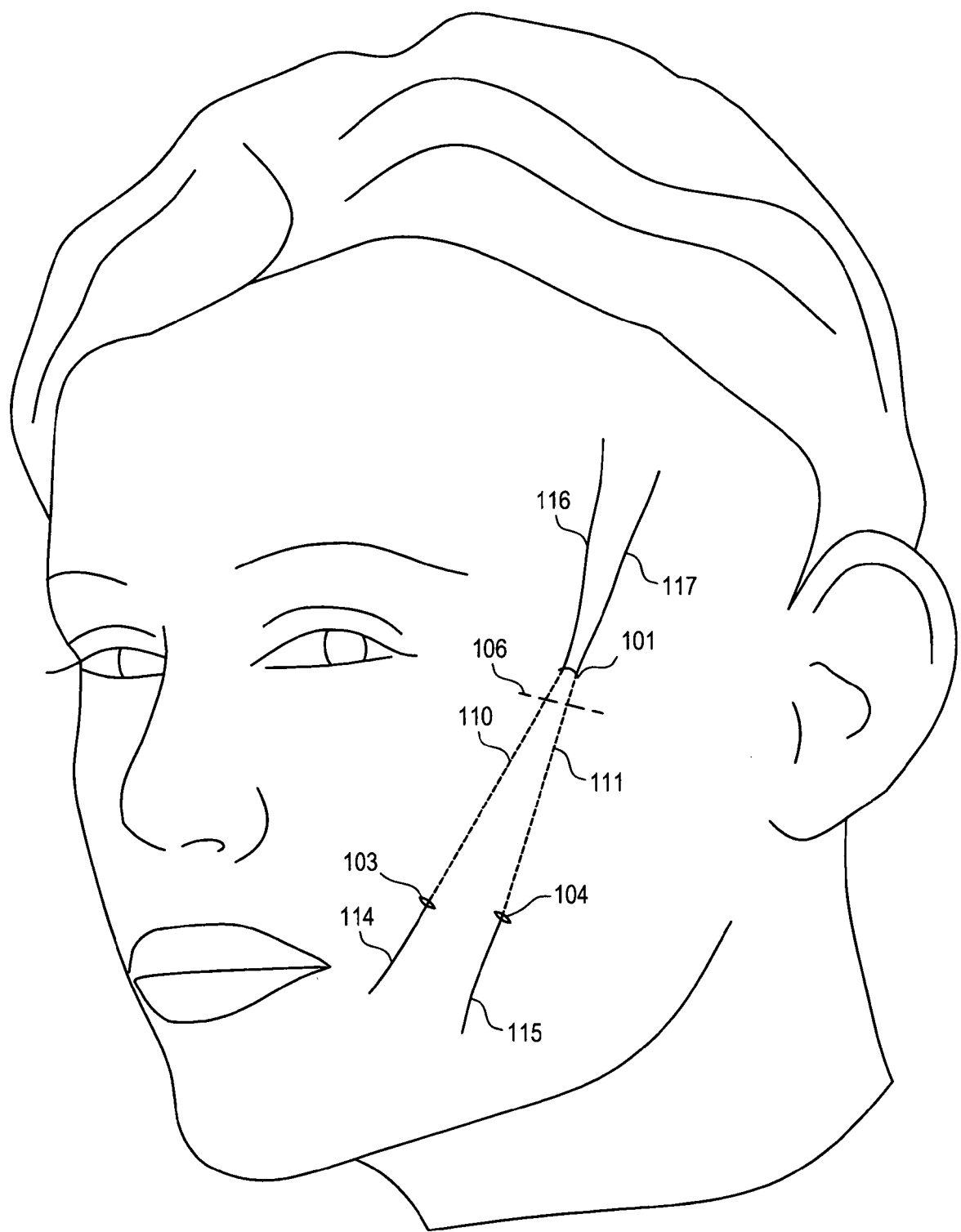

Referring next to FIG. 16, and following withdrawal of the tether insertion device 50 from the entry puncture 101, the tether 110 will extend from the exit puncture 103 and the tether 111 will extend from the exit puncture 104. Both of the tethers 110, 111 will extend from the entry puncture 101. In addition, the tether 110 will pass through the periosteum 106 while the tether 111 passes superficial to the periosteum 106, which then allows the periosteum to be used as a strong rung (or loop) which can serve as a local, natural anchor for receiving a tissue-supporting sling, as will be described more fully below. As alternatives, the tether 111 can pass through the periosteum 106, and the tether 110 can either pass through the periosteum 106 along a different pathway, or superficial to the periosteum 106.

Using the periosteum as a local anchoring point avoids the need for remote anchoring, such as in the skull behind the hair line. This, in turn, avoids the need to penetrate inside the temple region, where several nerves are present, which is potentially dangerous and preferably eliminated. This also avoids the need for long sutures, and the use of anchoring hardware such as nails or screws, as well as the need for expensive and complicated endoscopic instrumentation.

The resulting anchoring point is established without requiring any incisions and without requiring the use of other standard techniques, such as "undermining", for separating layers of subcutaneous tissue and for relieving portions of the fat layer to create pathways for freeing up layers of subcutaneous tissue. This further aids in reducing trauma to the patient during the surgical procedure being performed.

Figure 17:
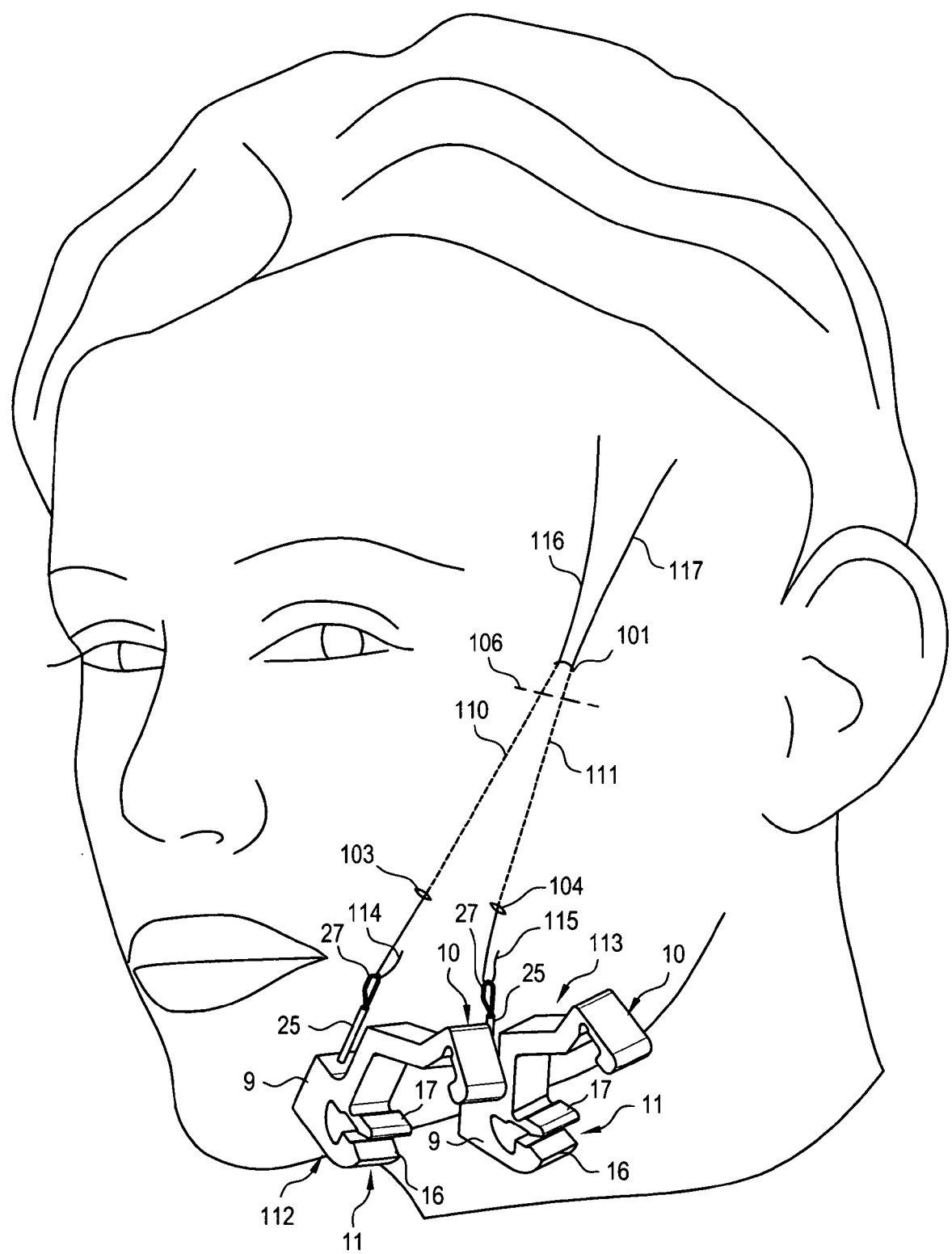
FIGS. 17 through 27 are sequential illustrations providing an example of one of the surgical procedures which can be performed in accordance with the present invention using the suture insertion device.

Referring next to FIG. 17, the eyelets 27 associated with a pair of housings 112, 113 are then loosely positioned over the face, adjacent to the exit punctures 103, 104. The ends 114, 115 of the tethers 110, 111 are then each respectively connected to the eyelet 27 of a housing 112, 113, preferably by tying the ends 114, 115 of the tethers 110, 111 to the eyelets 27 of the housings 112, 113.

Figure 18:
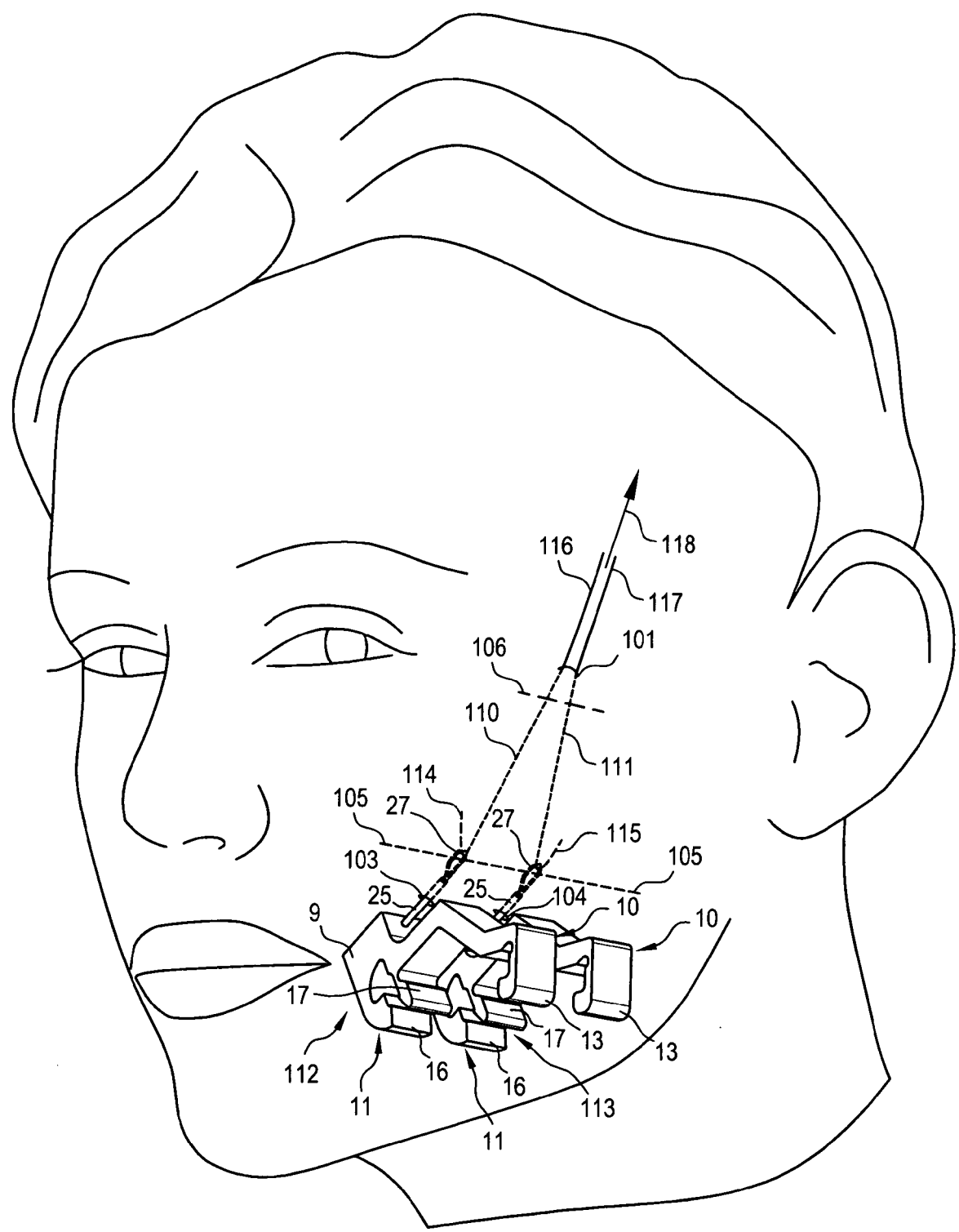

Referring next to FIG. 18, the opposing ends 116, 117 of the tethers 110, 111 are drawn in the direction of the arrow 118, placing tension on the eyelets 27 coupled with the opposing ends 114, 115 of the tethers 110, 111. This, in turn, draws the tethers 110, 111, and the associated eyelets 27 of the housings 112, 113, into the exit punctures 103, 104. Continued retraction of the tethers 110, 111 draws the eyelets 27 of the housings 112, 113 through the subcutaneous tissue and toward the centerline 105, which develops the intended "lift line" for the surgical procedure to be performed. Use of the tethers 110, 111 to draw the eyelets 27 of the housings 112, 113 into the exit punctures 103, 104 and to the centerline 105 is preferred to guide the elongate members 25 along the subcutaneous pathways previously established when positioning the tethers 110, 111 using the tether insertion device 50. Otherwise, the ends of the elongate members 25 would be left free to wander, or possibly bend from their intended pathways during insertion.

Figure 19:
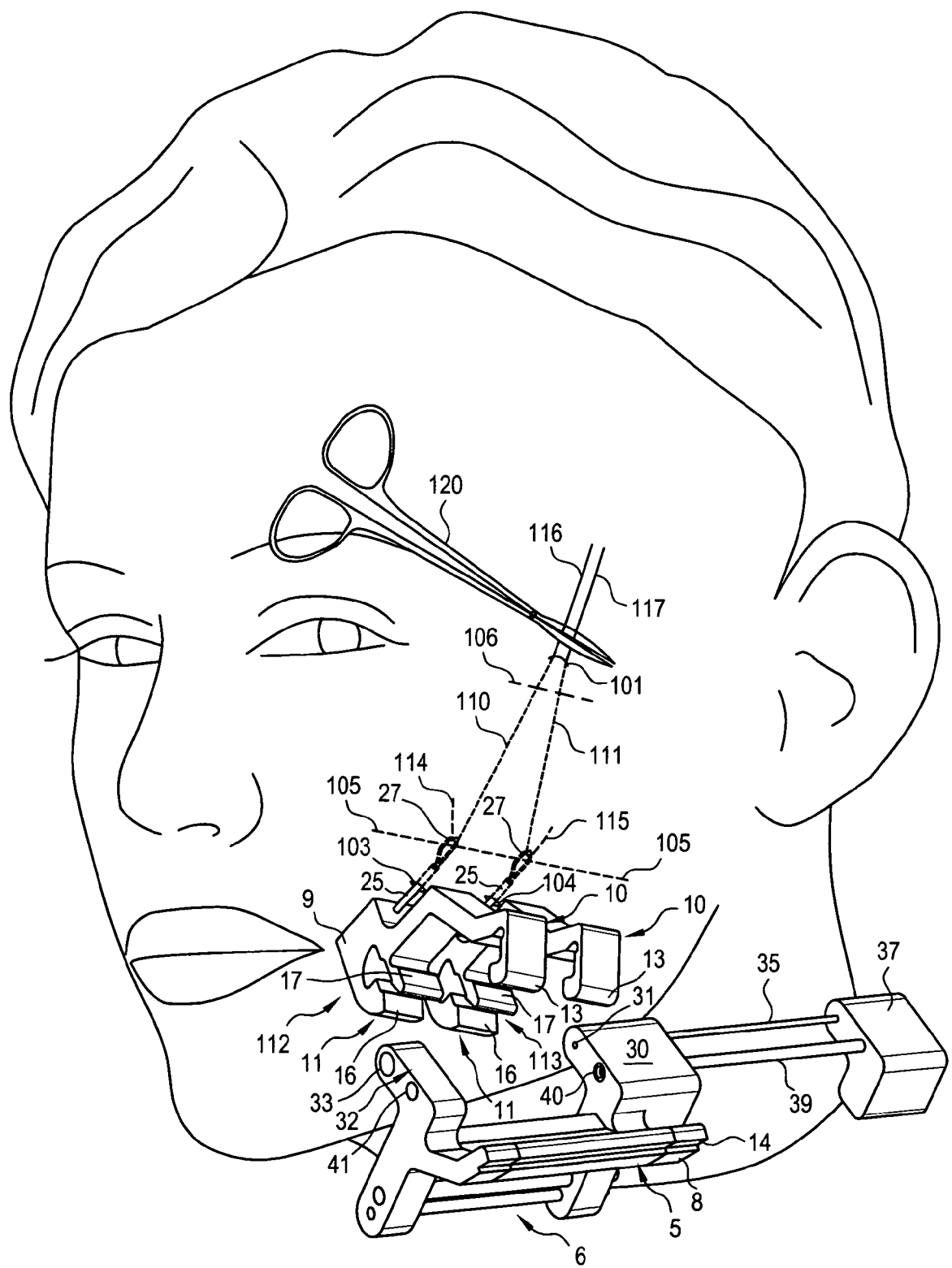

Referring next to FIG. 19, a hemostat 120 is preferably used to clamp the tethers 110, 111 in position, in turn maintaining the positioning previously established for the eyelets 27 and the housings 112, 113. The suture insertion device 1 is then positioned adjacent to the housings 112, 113.

Figure 20:
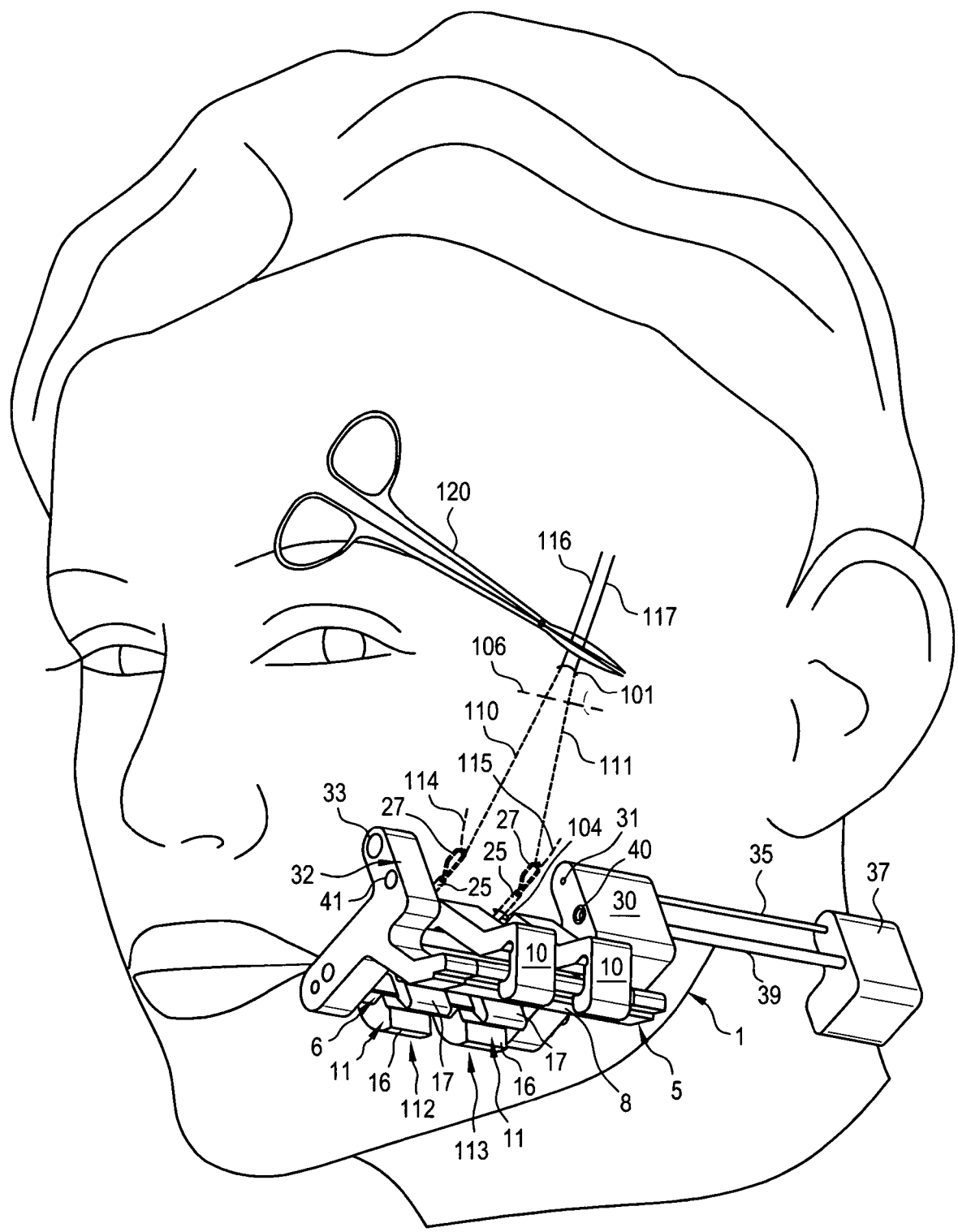

As described previously, the fingers 16, 17 are first passed over the rods 6, facilitated by the sloping surfaces 19, so the rods 6 pass through the openings 18 and into the cavities 20. The housings 112, 113 are then rotated, which in turn brings the catches 13 into engagement with the flange 8 of the alignment member 5 of the suture insertion device 1. The housings 112, 113 are in this way adjustably mated with the suture insertion device 1, and are placed in secure engagement with the suture insertion device 1, as is shown in FIG. 20.

Attachment of the housings 112, 113 to the suture insertion device 1 establishes the appropriate extension of the eyelets 27 relative to the centerline 105 and allows the housings 112, 113 to be positioned along the alignment members 5, 6 to accommodate the spacing between the exit punctures 103, 104 that receive the elongate members 25. In this way, the elongate members 25 are readily adapted to the site, and the surgical procedure which is being performed, and the eyelets 27 are automatically positioned concentrically with the common centerline 105. This reduces the amount of accuracy required for initial guidance of the tether insertion device 50, and for establishing the separation between the exit punctures 103, 104.

Figure 21:
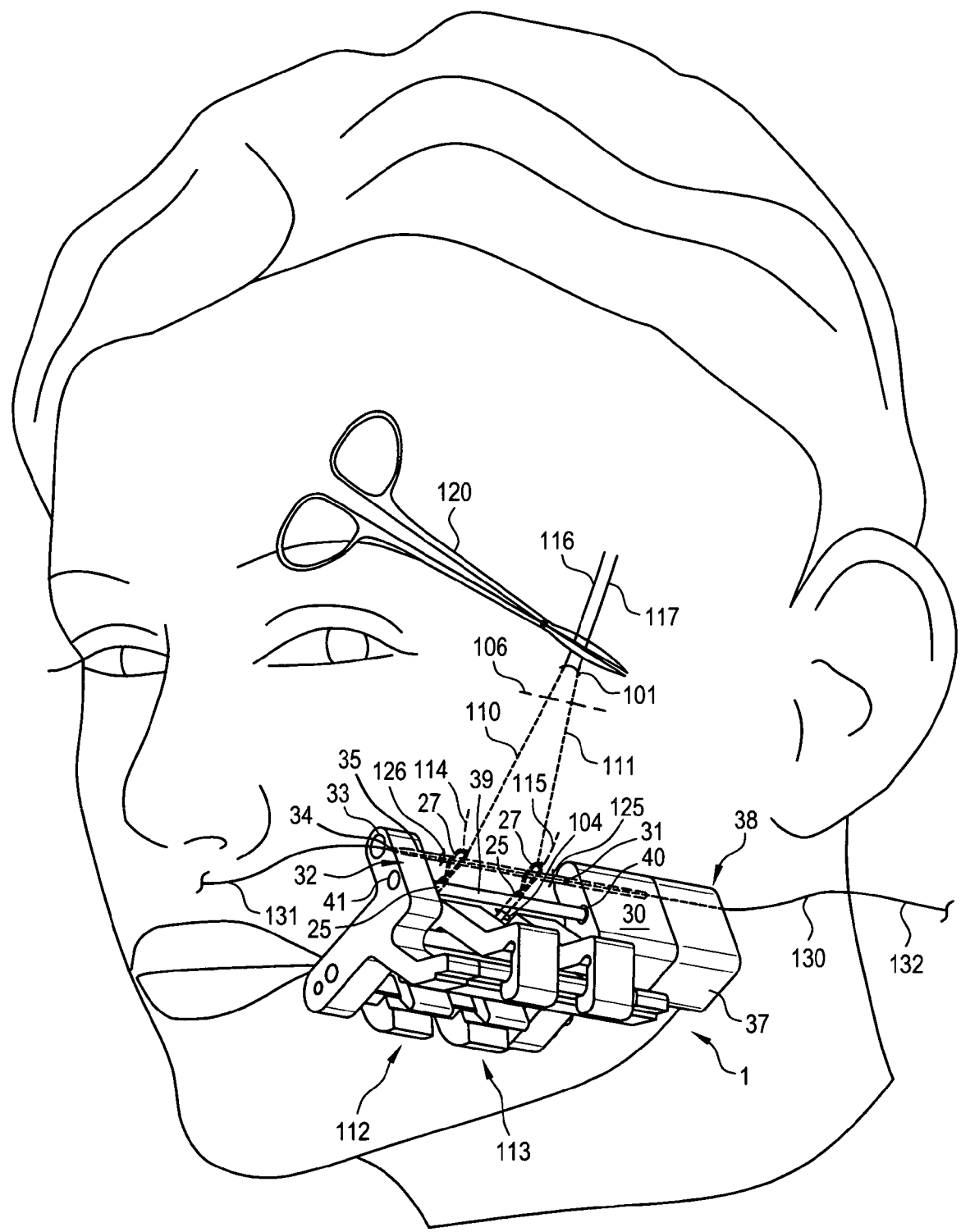

Referring next to FIG. 21, the actuator 37 is used to advance the needle 35 of the suture insertion device 1 through the guide 30 and along the centerline 105. Interaction between the rod 39 and the aperture 40 formed in the guide 30 provides additional structural support for guidance of the needle 35 along the centerline 105. Such advancement of the needle 35 causes the distal tip 34 to penetrate the skin, at a first puncture 125, passing subcutaneously beneath the skin and through the eyelets 27 of the elongate members 25 associated with the housings 112, 113. Continued advancement of the needle 35 again causes the distal tip 34 to penetrate the skin, exiting from a second puncture, at 126, and entering the guard 32 to prevent prick injury to the user of the suture insertion device 1. Subcutaneous passage of the needle 35 along the centerline 105 is automatically guided by the aligning structures of the suture insertion device 1, ensuring effective passage of the needle 35 along the centerline 105 and through the eyelets 27.

After the needle 35 has been fully advanced through the guide 30 and into the guard 32 of the suture insertion device 1, a suture 130 is threaded completely through the needle 35. The use of 3-0 polypropylene suture material is presently considered preferred. Other suture materials can also be used, if desired, or appropriate for a particular surgical procedure. As a further alternative, sutures having enlarged, tissue-supporting sections, such as the sutures 80, 85 shown in FIGS. 9 and 10, can be used to help distribute lifting stresses on subcutaneous tissue.

Threading of the suture 130 can be performed from either end of the needle 35. Entry of the suture 130 into the needle 35 is preferably assisted by shaping the proximal end 38 of the needle 35. To this end, the actuator 37 can be provided with a taper at the point of entry to the proximal end 38 of the needle 35, as previously described. If a conventional cannula is used to provide the functionality of the needle 35, the cannula can be provided with a hub to provide a smooth tapered entrance to the cannula. As a further alternative, a suture having an attached needle or shaft (e.g., by swaging) can be used. In such case, a tapered guide for entering the needle 35 would not be needed. However, the attached needle would then have to be removed from the suture after passing through the needle 35 and the suture insertion device 1. If a suture having tissue-engaging portions is used, such as the sutures 80, 85 shown in FIGS. 9 and 10, the suture can be attached to the outer portions of a standard needle, as previously described, in cases where the enlarged portions of the suture cannot be passed through a hollow needle structure.

Figure 22:
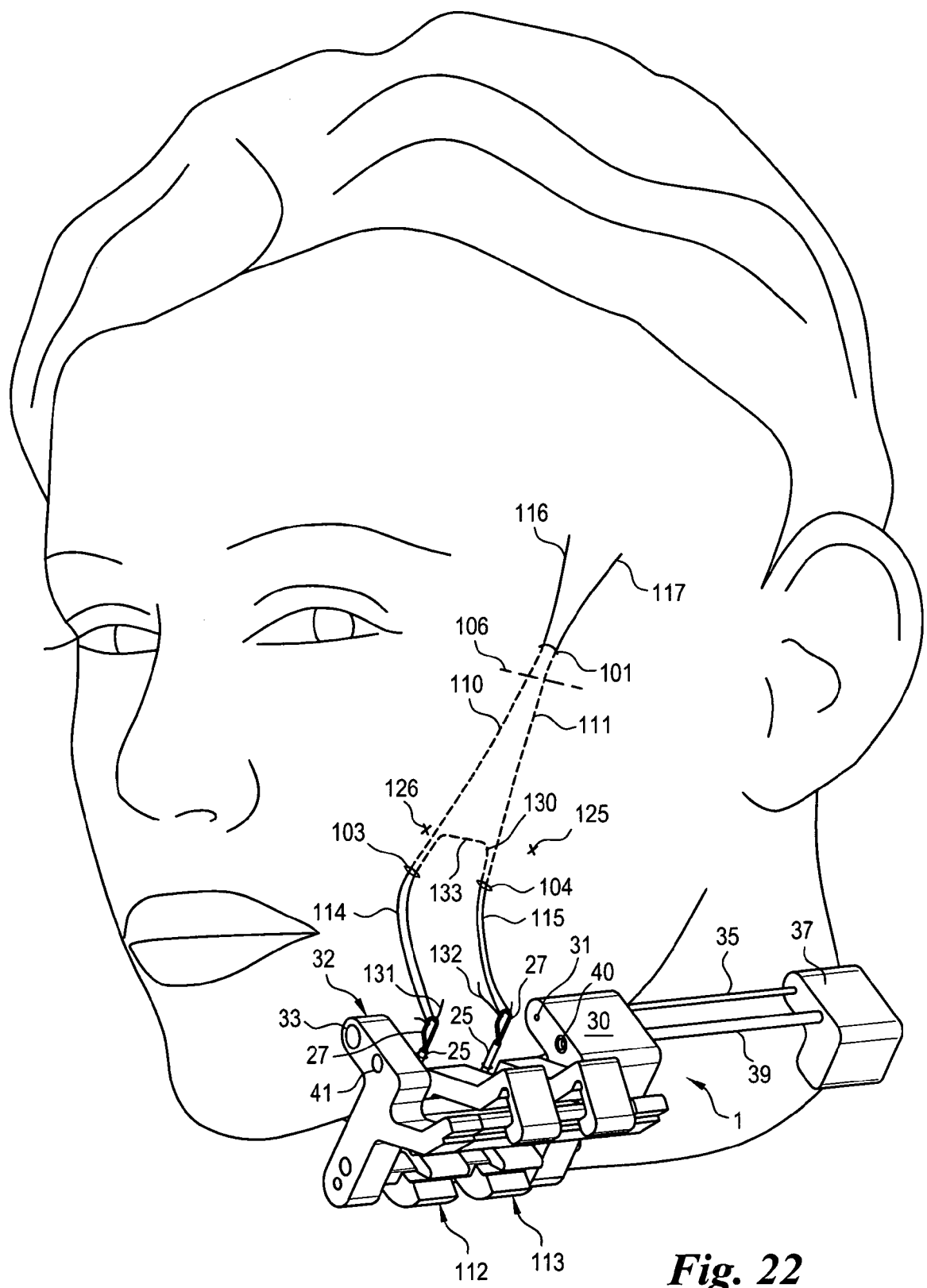

Referring next to FIG. 22, the actuator 37 is used to return the needle 35 to its initial, retracted position, while grasping a free end 131 of the suture 130 to prevent withdrawal of the suture 130. This causes the distal tip 34 of the needle 35 to withdraw from the guard 32, to withdraw from the second puncture, at 126, to pass subcutaneously beneath the skin, exiting from the eyelets 27 associated with the housings 112, 113, and to withdraw from the first puncture, at 125, preferably coming to rest inside the aperture 31 of the guide 30 to prevent prick injury to the user of the suture insertion device 1. This then releases the suture insertion device 1 from the face of the patient, except for the eyelets 27 and the elongate members 25, which remain seated within the exit punctures 103, 104. The suture 130 will then remain in place, extending from the punctures 125, 126 and beneath the skin.

The elongate members 25 associated with the housings 112, 113 are then drawn downwardly, as is shown in FIG. 22, pulling the elongate members 25 from the exit punctures 103, 104. This, in turn, pulls down portions of the suture 130 engaged by the eyelets 27 of the elongate members 25, and the tethers 110, 111 which remain tied to the eyelets 27, which then pass through the exit punctures 103, 104.

Before the ends 116, 117 of the tethers 110, 111 are pulled through the entry puncture 101, the ends 114, 115 are detached (cut or untied) from the eyelets 27 of the elongate members 25 so the ends 116, 117 of the tethers 110, 111 remain extended from the entry puncture 101 while the ends 114, 115 of the tethers 110, 111 remain extended from the exit punctures 103, 104. Continued movement of the suture insertion device 1 draws the opposing ends 131, 132 of the suture 130 from the exit punctures 103, 104, as is shown in FIG. 22.

Figure 23:
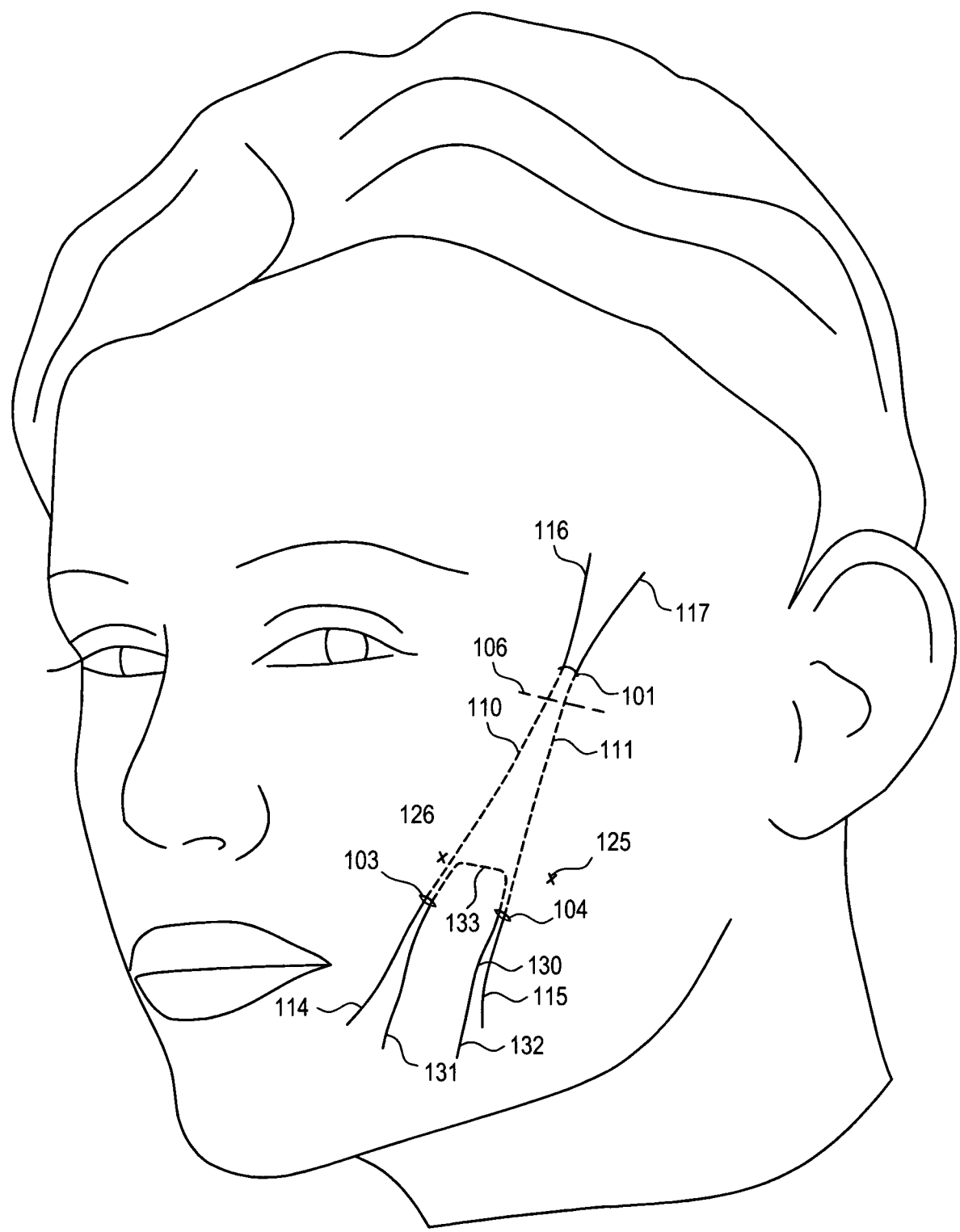
Figure 24:
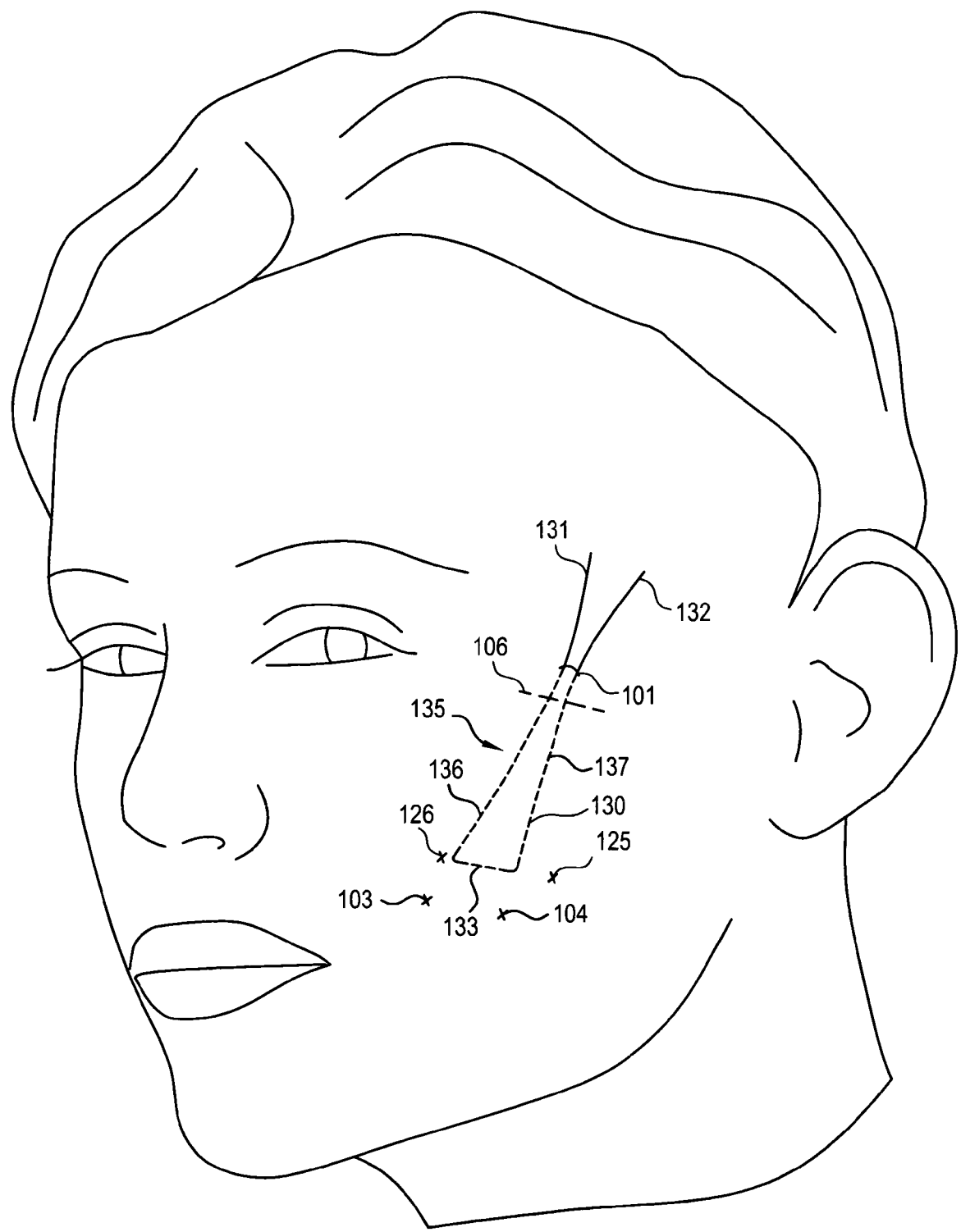

Referring next to FIG. 23, the opposing ends 131, 132 of the suture 130 are eventually pulled from the eyelets 27 and are released from the suture insertion device 1. Upon removal of the suture insertion device 1, the suture 130 is caused to assume the shape of an inverted "U" having center portions 133 embedded within subcutaneous tissue, and end portions 131, 132 extending from the exit punctures 103, 104. The free ends 131, 132 of the suture 130 are then tied to the free ends 114, 115 of the tethers 110, 111, respectively, and the ends 116, 117 of the tethers 110, 111 are then retracted to draw the ends 131, 132 of the suture 130 through the exit punctures 103, 104 and through the malar fat pad 100, eventually exiting from the entry puncture 101, as is shown in FIG. 24. This then leaves the center portions 133 of the suture 130 embedded within the subcutaneous tissue, at the intended lift line for the surgical procedure being performed, with free ends 131, 132 extending from the entry puncture 101 to form a triangular, tissue-supporting sling at 135.

Figure 25:
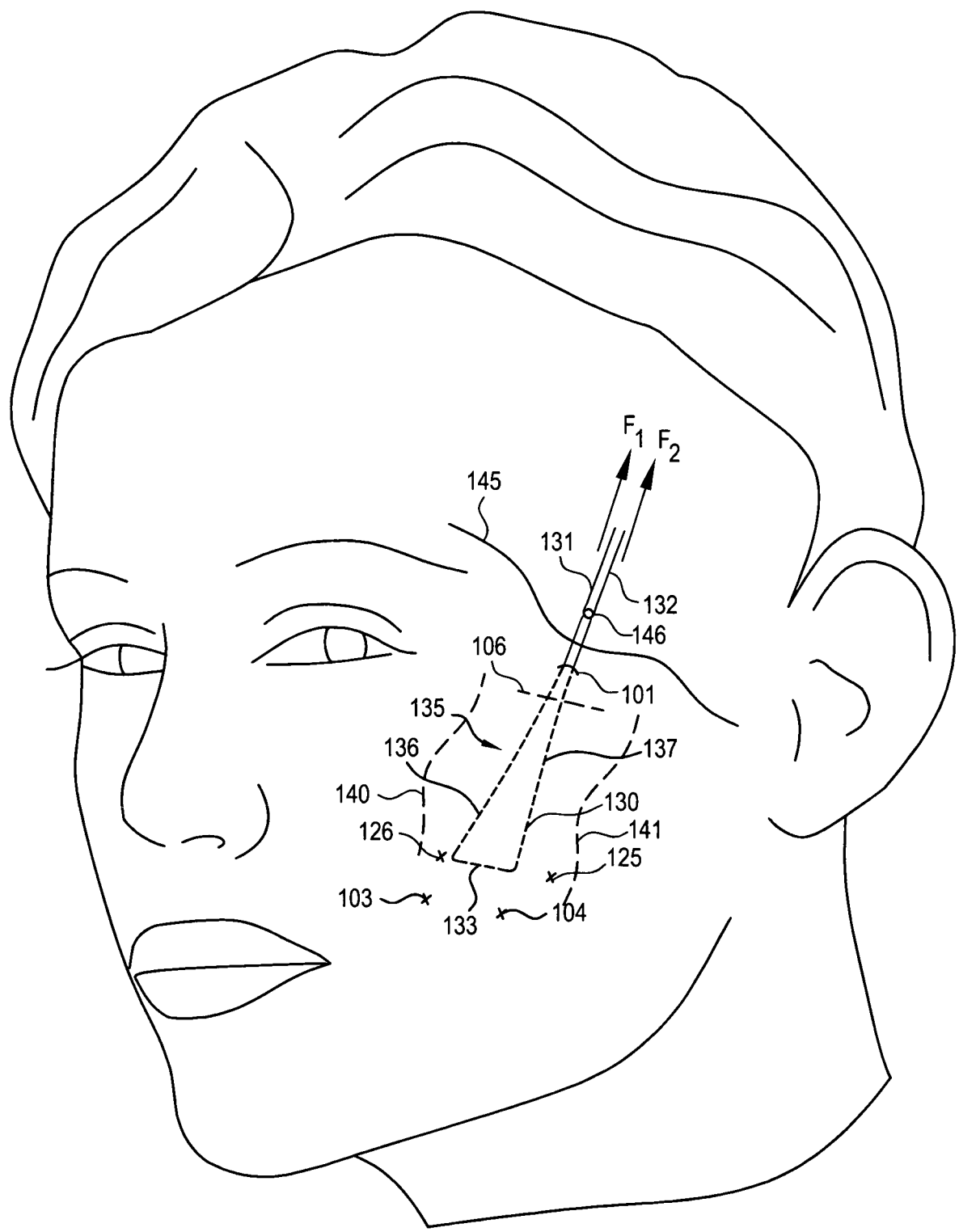

Referring next to FIG. 25, it will be seen that the ends 131, 132 of the suture 130 extend from the entry puncture 101 above the previously established formation in the periosteum 106. The periosteum 106 can then serve as a rung of strong tissue for anchoring the tissue-supporting sling 135 when, with appropriate tensioning, the sub-periosteum portion 136 of the suture 130 is tied to the portion 137 of the suture 130 which is then superficial to the periosteum 106.

To this end, tensioning forces F1 and F2 are applied to the ends 131, 132 of the suture 130, lifting the center portions 133 to achieve an appropriate amount of bunching of subcutaneous tissue within the malar fat pad 100, which is schematically shown at 140, 141, to achieve the desired facial contour. A hemostat can be used to engage the ends 131, 132 of the suture 130 to temporarily maintain this setting until the appropriate amount of lift is established. After the appropriate amount of lift has been established, the ends 131, 132 of the suture 130 can be tied off against the supporting rung of the periosteum 106, as is shown in FIG. 26.

Figure 26:
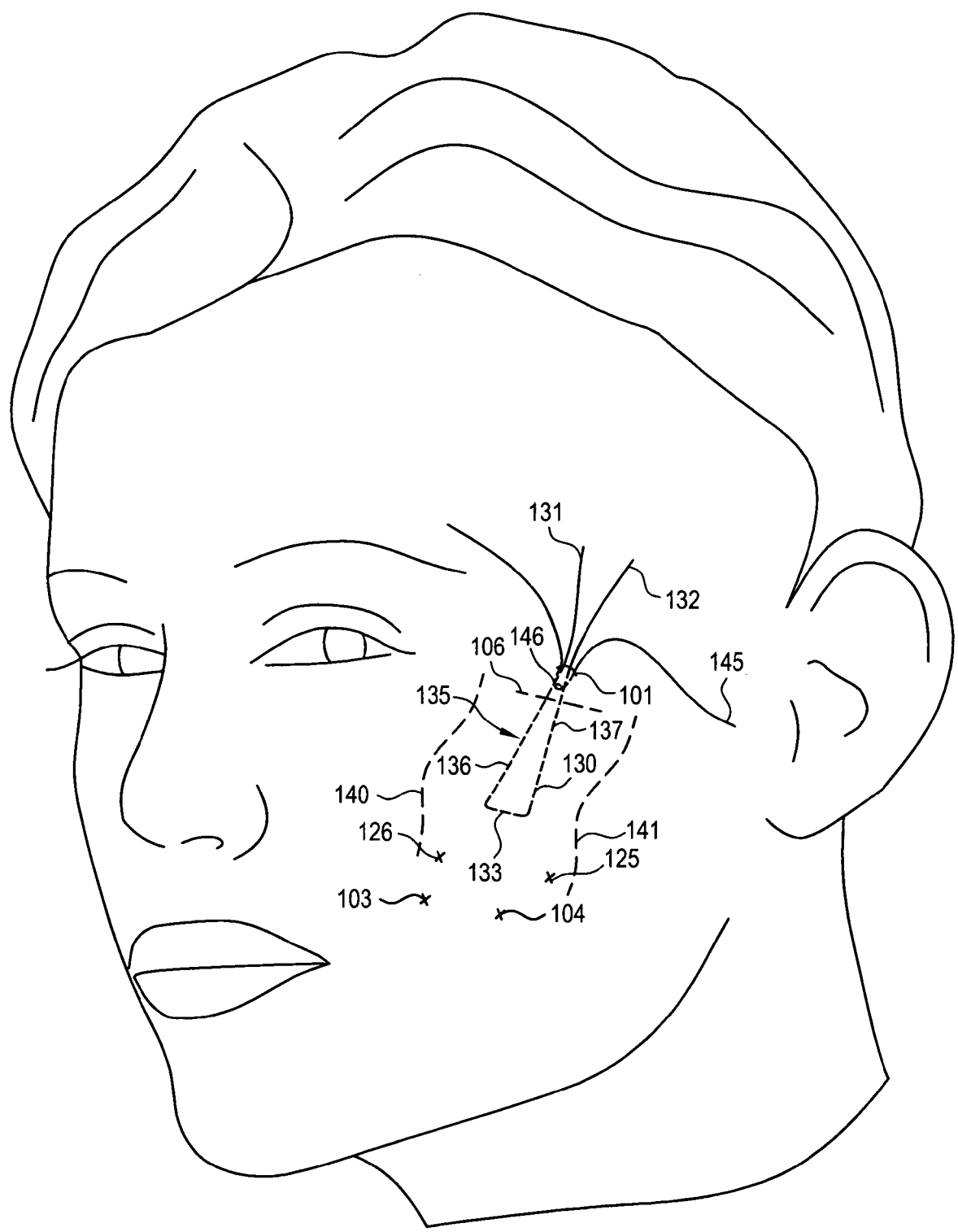

FIGS. 25 and 26 further show a temporary correction line 145 which is preferably used to facilitate appropriate tensioning of the tissue-supporting sling 135, as previously described. In use, the correction line 145 is positioned between the free ends 131, 132 of the suture 130 which extend from the entry puncture 101, and a first throw, shown at 146, is made to the ends 131, 132 of the suture 130 above the correction line 145. Referring to FIG. 26, the first throw 146 is tightened to achieve desired contouring, as previously described, drawing the first throw 146 and a portion of the correction line 145 inside the entry puncture 101 to rest against the supporting rung of the periosteum 106. The correction line 145 can then be used to loosen the first throw 146 in cases where an over-tightened sling 135 needs to be relieved.

A "granny knot" (or slip knot) can be made on a second throw of the ends 131, 132 of the suture 130, if desired, to temporarily secure the sling 135. The correction line 145 can be used to unslip the granny knot, to allow retensioning of the sling 135. Following appropriate tensioning of the sling 135, the correction line 145 can be removed either by sliding it from the knot or by cutting it off. As an alternative, the correction line 145 can be left in place, and can be tied over and/or around the knot for securing the sling 135, to provide the function of a knot-seizing line.

Figure 27:
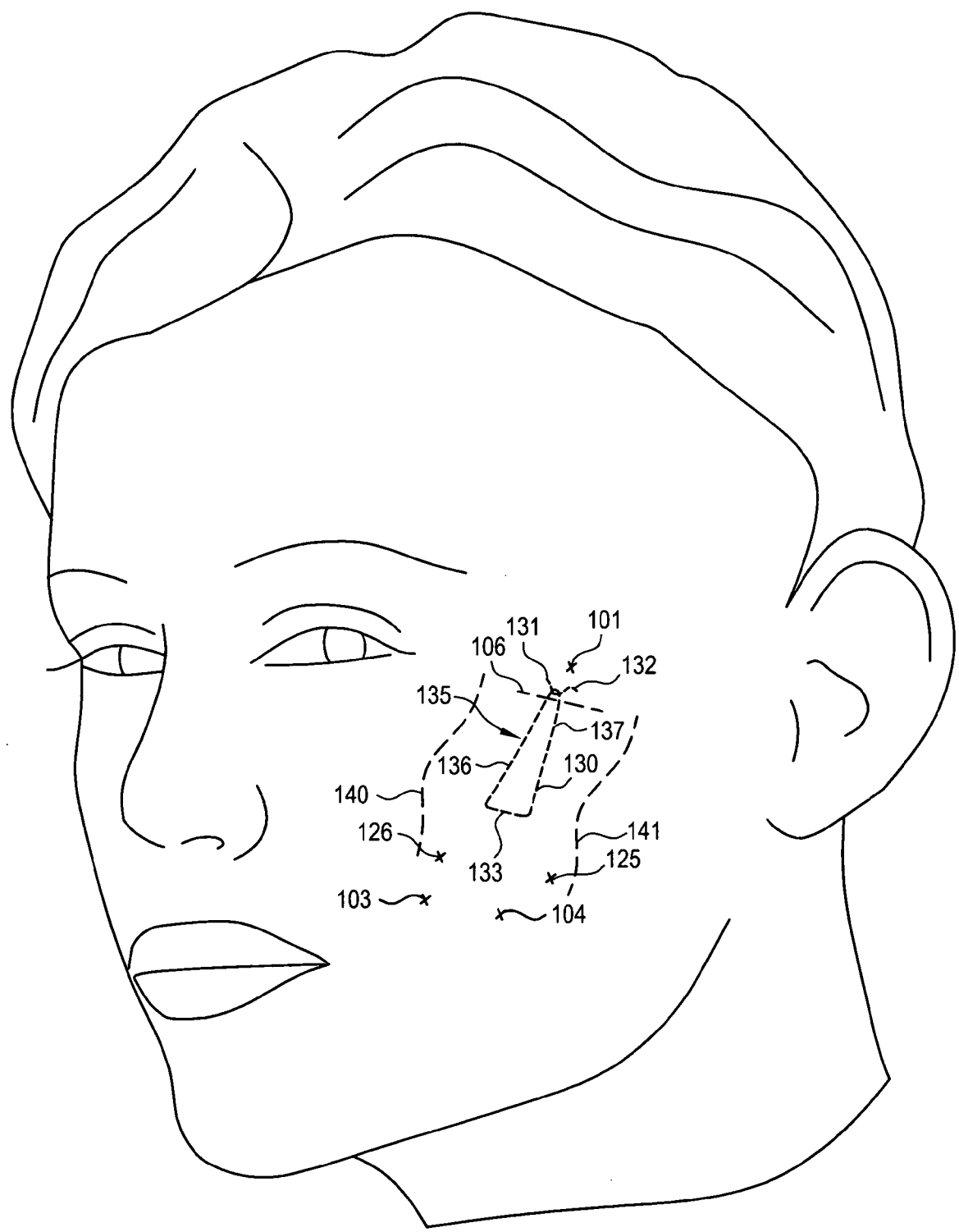

Referring next to FIG. 27, and after the ends 131, 132 of the suture 130 have been tied off against the supporting rung of the periosteum 106, with or without use of the correction line 145, a series of surgeon knots (square knots) can be made to secure the assembly. The ends 131, 132 of the suture 130 are then cut off and the resulting knot is positioned inside the entry puncture 101. The punctures 101, 103, 104, 125, 126 are then clear of all structures, which then leaves only the punctures 101, 103, 104, 125, 126 to close and heal following the surgical procedure. Because the several punctures are made with narrow gage needles, such punctures can close and heal virtually immediately.

Variations of the above-described surgical procedure are also possible. For example, the tissue-engaging sutures 80, 85 shown in FIGS. 9 and 10 can be used in place of conventional sutures, to form the sling 135 shown in FIG. 27. Use of the suture 80, 85 serves to position modified portions 83 of the suture 80, 85 within the subcutaneous tissue, providing added reinforcement along the portions of the suture 80, 85 which include the modified portions 83.

Another variation of the above-described surgical procedure makes use of elongate members 25 that are capable of being separated from the housings 112, 113. Initially, the same procedures described with reference to FIGS. 11 to 21 would be performed, leaving the suture insertion device 1 installed, as is shown in FIG. 21, with the elongate members 25 passing through the exit punctures 103, 104 and with the threaded suture 130 passing through the needle 35.

Figure 28:
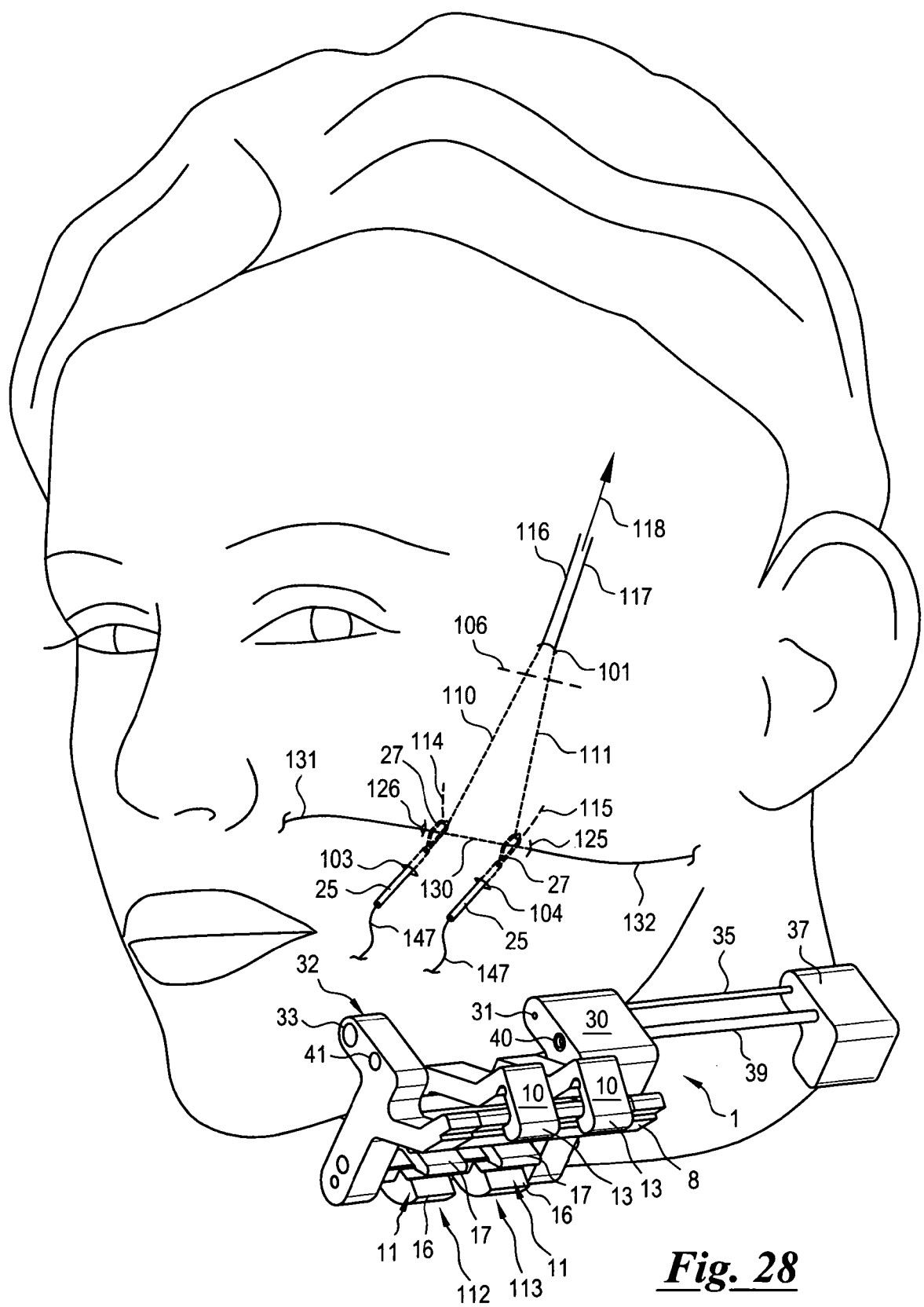
FIGS. 28 through 30 are sequential illustrations providing an example of one of the surgical procedures which can be performed in accordance with the present invention using an alternative embodiment suture insertion device having detachable eyelets.

Referring next to FIG. 28, the actuator 37 is once again used to return the needle 35 to its initial, retracted position, while grasping the free end 131 of the suture 130 to prevent withdrawal of the suture 130, causing the distal tip 34 of the needle 35 to withdraw from the guard 32, to withdraw from the second puncture, at 126, to pass subcutaneously beneath the skin, exiting from the eyelets 27 associated with the housings 112, 113, and to withdraw from the first puncture, at 125, preferably coming to rest inside the aperture 31 of the guide 30 to prevent prick injury to the user of the suture insertion device 1. Once again, this releases the suture insertion device 1 from the face of the patient, except for the eyelets 27 and the elongate members 25, which remain seated within the exit punctures 103, 104, and the suture 130, which then remains in place, extending from the punctures 125, 126 and beneath the skin.

The elongate members 25 associated with the housings 112, 113 are then detached from the housings 112, 113, as previously described. The suture insertion device 1 is then removed, leaving the elongate members 25 extending from the exit punctures 103, 104. The tethers 110, 111 also then remain attached to the eyelets 27.

The ends 116, 117 of the tethers 110, 111 are drawn in the direction of the arrow 118, placing tension on the eyelets 27 coupled with the opposing ends 114, 115 of the tethers 110, 111. This, in turn, draws the elongate members 25 through the exit punctures 103, 104, as is shown in FIG. 29.

Figure 29:
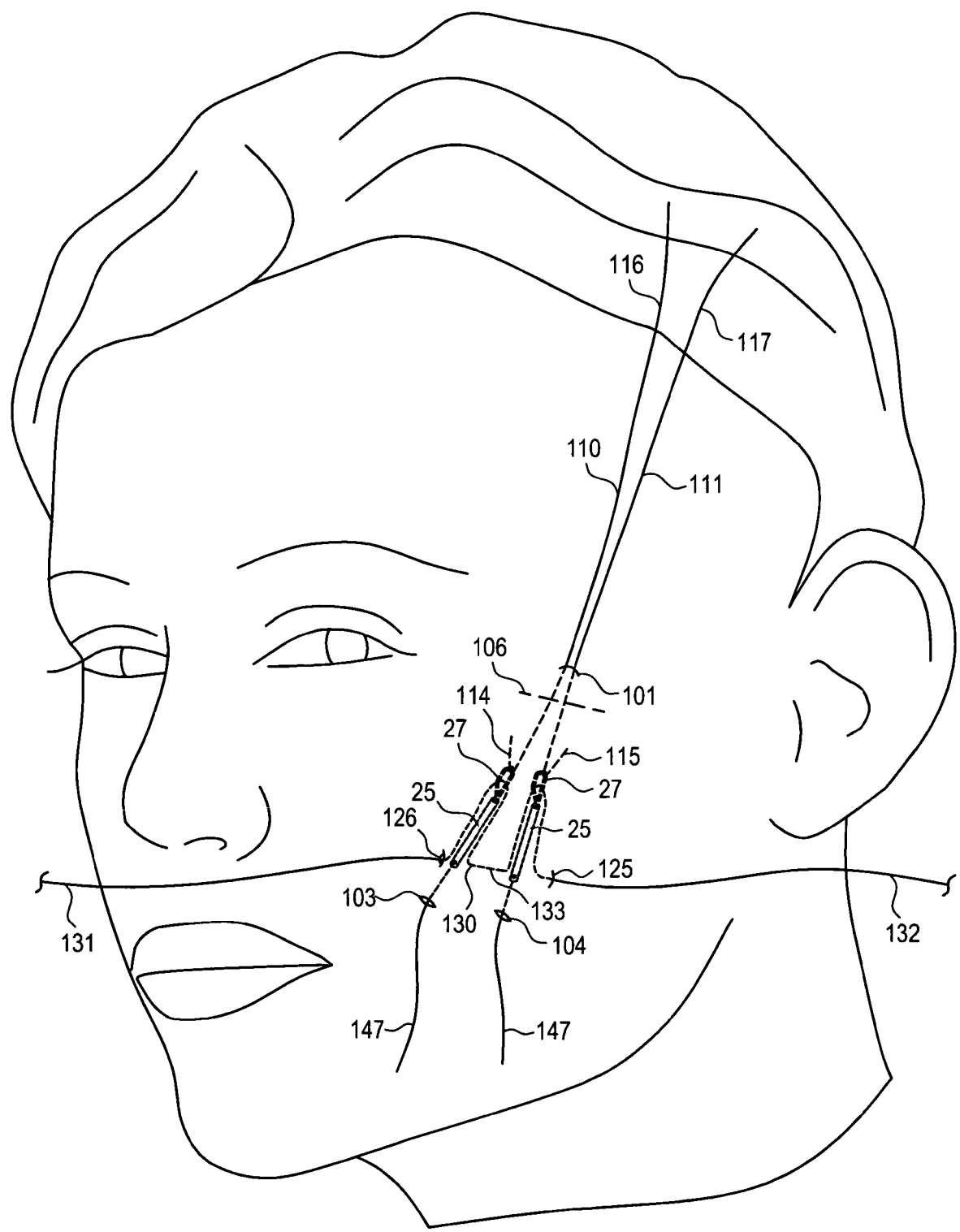

Referring next to FIG. 29, continued retraction of the tethers 110, 111 pulls the elongate members 25 upwardly, through the malar fat pad 100 and to the rung in the periosteum 106, along the subcutaneous pathways previously established when positioning the tethers 110, 111 using the tether insertion device 50. This, in turn, pulls portions of the suture 130 engaged by the eyelets 27 of the elongate members 25 upwardly, eventually passing the periosteum 106 and through the entry puncture 101, as is shown in FIG. 30.

The elongate members 25 are preferably pulled through the entry puncture 101 one at a time to prevent trauma. Lines 147 can be attached to the elongate members 25 and, if desired, can pass through the apertures 29 provided in the housings 7, for retrieving a detached elongate member 25 which has become embedded in subcutaneous tissue.

Figure 30:
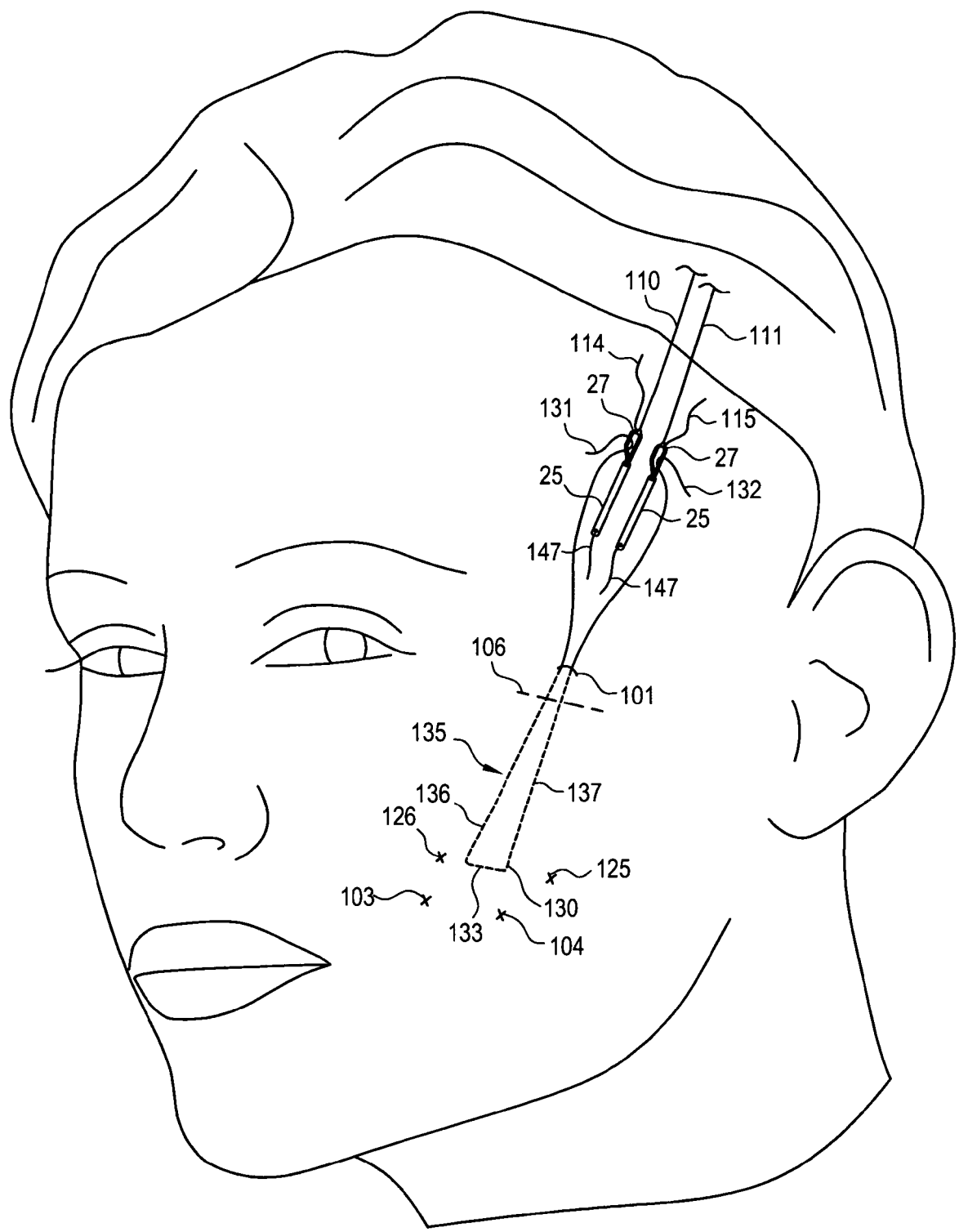

Referring next to FIG. 30, and after the elongate members 25 have been fully withdrawn from the entry puncture 101, a subcutaneous sling 135 is developed which includes a center section 133, a portion 136 which passes through the periosteum and a portion 137 which is superficial to the periosteum 106. The ends 131, 132 of the suture 130 are then removed from the eyelets 27, and the periosteum 106 can then serve as a rung of strong tissue for anchoring the sling 135 to support tissue as previously described. As similar result can be achieved by separating the eyelets 27 from the elongate members 25, as previously described.

As further alternatives, the previously described embodiments each make use of a pair of housings 7, 48, and a single elongate member 25 associated with each one of the housings 7, 48. It is also possible to associate more than one elongate member 25 with a single housing 7, 48 and/or to use either a single housing 7, 48, or more than two housings 7, 48, if preferred. More than one eyelet 27 can be associated with a single elongate member 25, if desired, or one or more eyelets 27 can be directly coupled with the body 2 of the suture insertion device 1, eliminating the need for separate housings 7.

Figure 31:
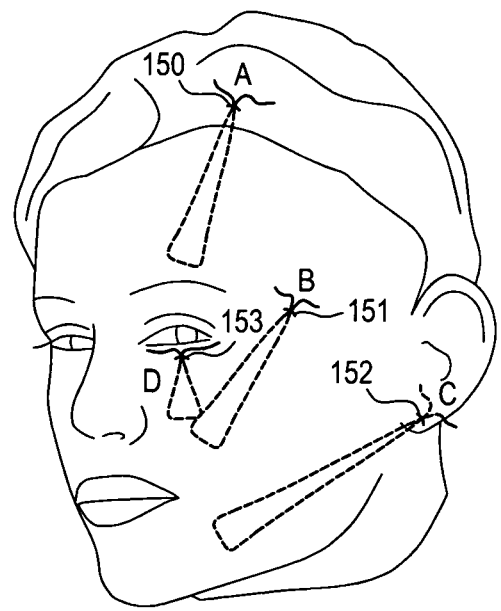
FIGS. 31 and 32 are illustrations showing various surgical procedures which can be performed in accordance with the present invention.
Figure 32:
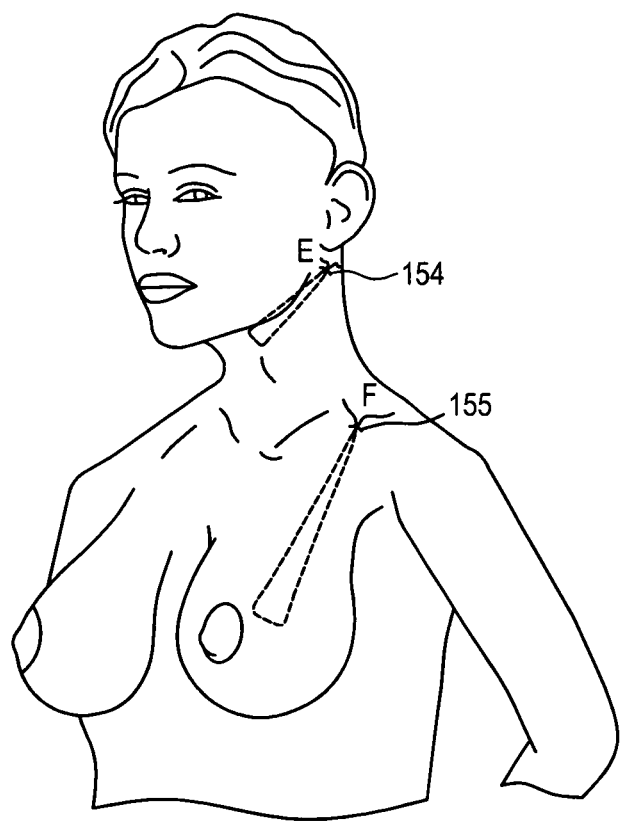

As further alternatives, FIG. 31 shows examples of some of the variety of other surgical procedures which can be performed using the above-described devices and methods. The placement of a suture sling 135 for performing a brow lift is shown in the region A, in combination with an entrance location 150. The placement of a suture sling 135 for performing a mid face lift is shown in the region B, in combination with an entrance location 151. The placement of a suture sling 135 for performing a chin lift is shown in the region C, in combination with an entrance location 152. The placement of a suture sling 135 for performing an under-eye lift is shown in the region D, in combination with an entrance location 153. FIG. 32 further shows the placement of a suture sling 135 for performing a neck lift, in the region E, in combination with an entrance location 154, and the placement of a suture sling 135 for performing a breast lift, in the region F, in combination with an entrance location 155.

For purposes of performing an under-eye lift, the suture insertion device selected for use can have elongate members which are shortened, or in the alternative, curved or bent, so the selected apparatus can fit into the relatively small spaces available. For purposes of performing a brow lift, the suture insertion device can have a curved or bent body so the selected apparatus can extend over the forehead of the patient.

The entrance locations 150, 151, 152, 153, 154 shown for the above-described lifts are typical, and are preferred because they are located in hidden places, such as above the hair line, or in the breast. However, because of the significantly reduced potential for trauma resulting from the absence of any incisions and the small size of the punctures 101, 103, 104, 125, 126, greater flexibility in the placement of the entrance locations 150, 151, 152, 153, 154 is afforded. Also, the anchoring procedures used in these locations can be different from the above-described procedures, if desired. The anchoring procedure used can be varied, as appropriate, and can include the use of a bone penetration channel, staples, screws, a ligament, a muscle or the like.

As a further alternative, and for any of the surgical procedures which can be performed using the suture insertion devices 1, 45, as previously described, one or more of the elongate members 25 can be replaced with an expandable eyelet of the type described in International Application No. PCT/US2008/009012. In such cases, the expandable eyelet can be selectively deployed via the aperture 29 provided in housing 7, developing an eyelet which is expandable and contractible, for replacing the fixed eyelets 27.

As a further alternative, the straight needle 35 of the suture insertion devices 1, 45 shown in FIGS. 1 to 5 can be replaced with a shaped needle, for example, a needle having a curvature which bows in a desired direction for facilitating passage of the needle through the skin and through subcutaneous tissue. The various structures associated with such a suture insertion device can then be modified to ensure the appropriate longitudinal advancement of a shaped needle through the device, including modification of the shape and the orientation of the aperture 31 of the guide 30, the shape, orientation and location of the eyelets 27 of the elongate members 25, and the location of the open region 41 of the guard 32, if used.

Figure 33:
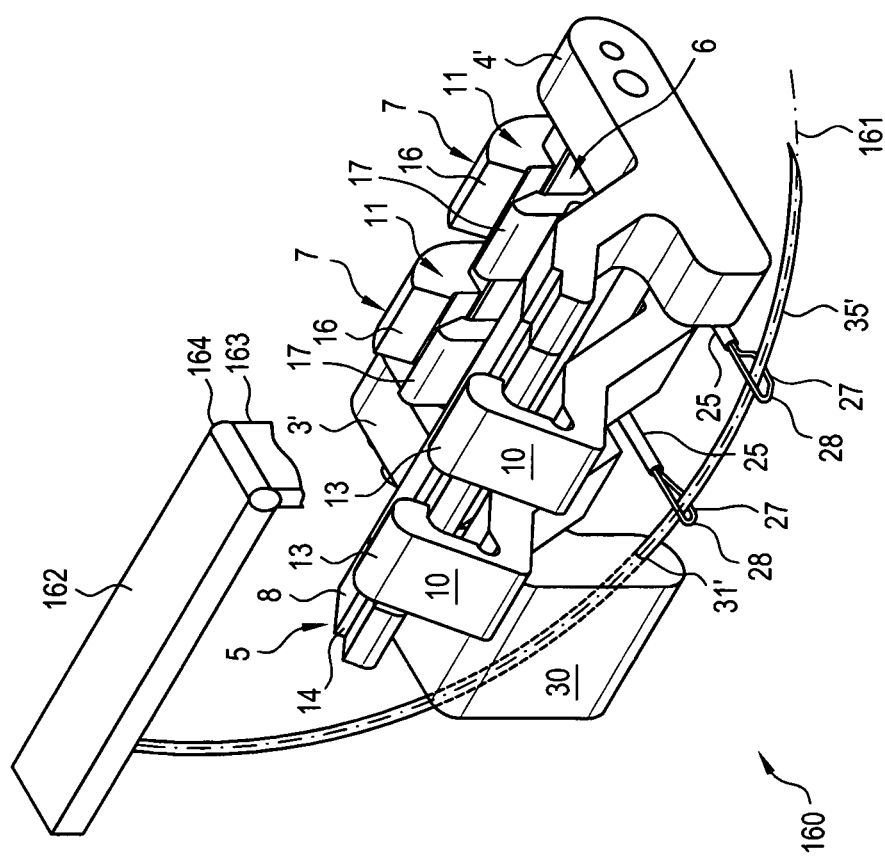
FIGS. 33 and 34 are isometric views showing further alternative embodiments of a suture insertion device produced in accordance with the present invention.
Figure 34:
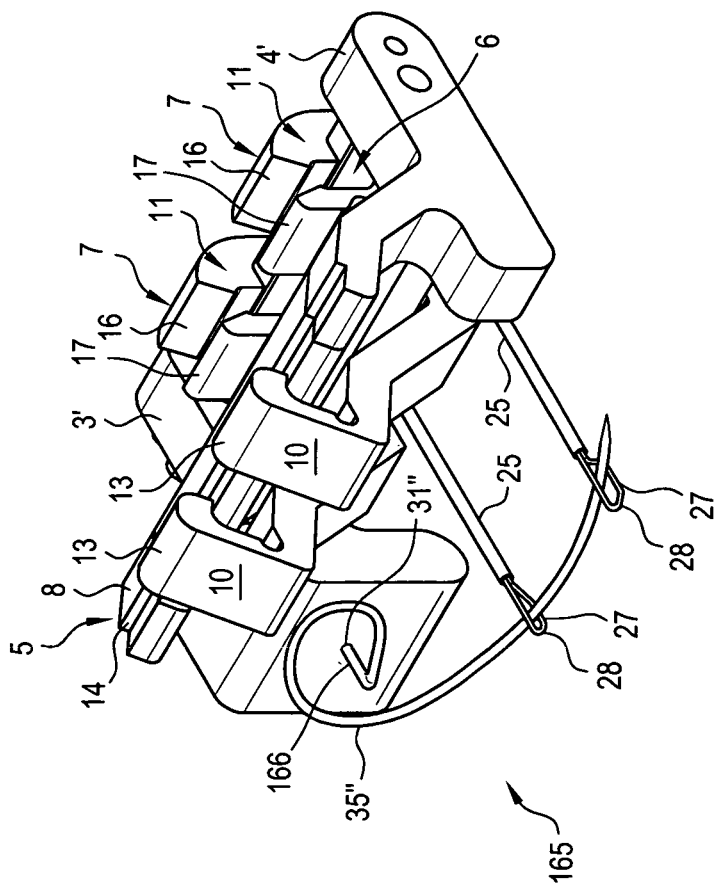

FIGS. 33 and 34 show alternative embodiments of the suture insertion devices 1, 45 shown in FIGS. 1 to 5. The configuration of the suture insertion devices shown in FIGS. 33 and 34 have various features in common with the suture insertion devices 1, 45 shown in FIGS. 1 to 5, but exhibit some variations. In the description which follows, components corresponding to those previously described have corresponding reference numbers.

FIG. 33 shows a suture insertion device 160 which replaces the straight needle 35 with a curved needle 35'. The guide 30 has been provided with a curved aperture 31' having a curvature which corresponds to the curvature of the needle 35', and the guard 32 has been removed from the arm 4'. Longitudinal advancement of the curved needle 35' through the aperture 31' of the guide 30 and along the curved centerline 161 causes the curved needle 35' to advance through the eyelets 27 associated with the elongate members 25. The eyelets 27 are preferably placed at an angle which is normal to the centerline 161 to facilitate entry of the curved needle 35' into the eyelets 27. Longitudinal advancement of the curved needle 35' along the centerline 161 can establish interaction with the skin and the subcutaneous tissue similar to the interaction established with the straight needle 35, and can further eliminate the need to depress tissue adjacent to the guide 30 to facilitate passage of the suture-feeding structure through the suture insertion device 160.

Advancement of the curved needle 35' along the centerline 161 can also facilitate operation of the suture insertion device 160 using a different type of actuator. The actuator 37 of the suture insertion devices 1, 45 shown in FIGS. 1 to 5 has been replaced with an actuator in the form of an arm 162. One end of the arm 162 is coupled with the needle 35' and the other end of the arm 162 is pivotally coupled with a support 163 associated with the body of the suture insertion device 160. The arms 162, 163 are coupled by a hinge 164 so that forces applied to the arm 162 can cause the curved needle 35' to advance and withdraw along the centerline 161.

FIG. 34 shows a suture insertion device 165 which replaces the curved needle 35' with a needle 35" having the overall form of a corkscrew. The guide 30 is provided with an aperture 31" having an orientation which is substantially perpendicular to the orientation of the apertures 31, 31'. The aperture 31" receives a pin 166 associated with the needle 35' so that movement of the needle 35" about the pin 166 will cause longitudinal advancement of the needle 35" through the eyelets 27 associated with the elongate members 25.

It will therefore be understood that while the present invention has been described based on specific embodiments incorporating specified parts, the present invention further encompasses all technical equivalents of the parts described, and that various changes in the details, materials, arrangement and combination of parts which have been herein described and illustrated in order to explain the nature of this invention may be made by those skilled in the art within the principle and scope of the invention as expressed in the following claims.

What is claimed is:

1. An apparatus for remotely and subcutaneously positioning a suture in tissue, wherein the apparatus comprises a body, an elongate member associated with and extending from the body, wherein a distal end of the elongate member includes an opening and wherein the opening is positioned to engage portions of the suture, and a guide associated with the body and spaced from the elongate member, wherein the guide includes a key and wherein the key is positioned to align the suture with a longitudinal axis extending through the opening of the elongate member, wherein the elongate member is coupled with a housing and wherein the housing is coupled with the body, and wherein the apparatus includes slidably detachable portions associated with the elongate member.

2. The apparatus of claim 1 wherein the key of the guide defines a longitudinal axis extending through the guide, and wherein the axis of the guide is aligned with the axis of the opening of the elongate member.

3. The apparatus of claim 1 wherein the key of the guide is an aperture including an extended passageway.

4. The apparatus of claim 1, in combination with a suture passing instrument having a shaft portion for passing the suture, wherein portions of the suture passing instrument are slidingly received by the key of the guide and in the opening of the elongate member.

5. The apparatus of claim 4 wherein the suture passing instrument is a narrow gage needle.

6. The apparatus of claim 5 wherein the suture passing instrument is a curved needle.

7. The apparatus of claim 5 wherein the needle has a distal tip which is slanted and oriented for engaging the opening of the elongate member.

8. The apparatus of claim 4 wherein proximal portions of the suture passing instrument are coupled with an actuator for advancing and retracting the suture passing instrument within the guide.

9. The apparatus of claim 8 which further includes a rod coupled with and extending between the actuator and the guide, for supporting the advancing and the retracting of the suture passing instrument within the guide.

10. The apparatus of claim 8 wherein the actuator is an arm coupled with the suture passing instrument and hingedly coupled with the body of the apparatus.

11. The apparatus of claim 4 which further includes a guard associated with and extending from the body.

12. The apparatus of claim 11 wherein the guide and the guard extend from opposing ends of the body.

13. The apparatus of claim 11 wherein the guard has an open region which is aligned with the axis of the opening, for receiving tip portions of the suture passing instrument.

14. The apparatus of claim 11 wherein the apparatus further includes a rod coupled with the suture passing instrument for supporting movements of the suture passing instrument within the guide, and wherein the guard has an open region which is aligned with a longitudinal axis extending through the rod, for receiving distal tip portions of the rod.

15. The apparatus of claim 11 wherein the guard is removably associated with the body.

16. The apparatus of claim 1 wherein the guide is removably associated with the body.

17. The apparatus of claim 1 which includes a single elongate member.

18. The apparatus of claim 1 which includes two, spaced elongate members.

19. The apparatus of claim 18 wherein each of the elongate members has an opening, and wherein the openings of the elongate members are aligned with the longitudinal axis.

20. The apparatus of claim 1 wherein the elongate member is detachably coupled with the housing.

21. The apparatus of claim 1 wherein the housing is adjustably coupled with the body, for moving the opening of the elongate member along the longitudinal axis.

22. The apparatus of claim 21 wherein the housing is adjustably coupled with spaced alignment members associated with the body.

23. The apparatus of claim 1 wherein the housing is detachably coupled with the body.

24. The apparatus of claim 1 wherein the opening for engaging portions of the suture is an elongated eyelet.

25. The apparatus of claim 1 wherein the opening for engaging portions of the suture is an eyelet, and wherein the eyelet is detachably coupled with the elongate member.

26. The apparatus of claim 1 wherein the opening for engaging portions of the suture is an expandable opening.

27. The apparatus of claim 1 wherein the elongate member defines a longitudinal axis extending along the elongate member, and wherein the longitudinal axis extending along the elongate member is different from the longitudinal axis extending through the opening of the elongate member.

28. The apparatus of claim 27 wherein the longitudinal axis extending along the elongate member intersects with the longitudinal axis extending through the opening of the elongate member.

29. The apparatus of claim 27 wherein the longitudinal axis extending along the elongate member forms an angle with the longitudinal axis extending through the opening of the elongate member.

30. The apparatus of claim 1 wherein the elongate member is associated with and extends from the body for passing through the tissue.

31. An apparatus for remotely and subcutaneously positioning a suture in tissue, wherein the apparatus comprises a body, wherein portions of the body include spaced alignment members, an elongate member associated with and extending from the body, wherein a distal end of the elongate member includes an opening and wherein the opening is positioned to engage portions of the suture, and a guide associated with the body and spaced from the elongate member, wherein the guide includes a key and wherein the key is positioned to align the suture with a longitudinal axis extending through the opening of the elongate member, wherein the elongate member is coupled with a housing and wherein the housing is adjustably coupled with the spaced alignment members of the body, for moving the opening of the elongate member along the longitudinal axis.

32. The apparatus of claim 31 which further includes a guard associated with and extending from the body.

33. The apparatus of claim 32 wherein the guide and the guard extend from opposing ends of the body.

34. The apparatus of claim 32 wherein the guard has an open region which is aligned with the axis of the opening, for receiving tip portions of a suture passing instrument.

35. The apparatus of claim 32 wherein the apparatus further includes a rod coupled with a suture passing instrument for supporting movements of the suture passing instrument within the guide, and wherein the guard has an open region which is aligned with a longitudinal axis extending through the rod, for receiving distal tip portions of the rod.

36. The apparatus of claim 32 wherein the guard is removably associated with the body.

37. The apparatus of claim 31 which includes a single elongate member.

38. The apparatus of claim 31 which includes two, spaced elongate members.

39. The apparatus of claim 38 wherein each of the elongate members has an opening, and wherein the openings of the elongate members are aligned with the longitudinal axis.

40. The apparatus of claim 31 wherein the opening for engaging portions of the suture is an elongated eyelet.

41. The apparatus of claim 31 wherein the opening for engaging portions of the suture is an expandable opening.

42. The apparatus of claim 31 wherein the elongate member defines a longitudinal axis extending along the elongate member, and wherein the longitudinal axis extending along the elongate member is different from the longitudinal axis extending through the opening of the elongate member.

43. The apparatus of claim 42 wherein the longitudinal axis extending along the elongate member intersects with the longitudinal axis extending through the opening of the elongate member.

44. The apparatus of claim 42 wherein the longitudinal axis extending along the elongate member forms an angle with the longitudinal axis extending through the opening of the elongate member.

45. The apparatus of claim 31, in combination with a suture passing instrument having a shaft portion for passing the suture, wherein portions of the suture passing instrument are slidingly received by the key of the guide and in the opening of the elongate member.

46. The apparatus of claim 45 wherein the suture passing instrument is a narrow gage needle.

47. The apparatus of claim 46 wherein the suture passing instrument is a curved needle.

48. The apparatus of claim 46 wherein the needle has a distal tip which is slanted and oriented for engaging the opening of the elongate member.

49. The apparatus of claim 45 wherein proximal portions of the suture passing instrument are coupled with an actuator for advancing and retracting the suture passing instrument within the guide.

50. The apparatus of claim 49 which further includes a rod coupled with and extending between the actuator and the guide, for supporting the advancing and the retracting of the suture passing instrument within the guide.

51. The apparatus of claim 49 wherein the actuator is an arm coupled with the suture passing instrument and hingedly coupled with the body of the apparatus.

52. The apparatus of claim 31 wherein the elongate member is receivable in the housing.

53. The apparatus of claim 52 wherein the elongate member is detachably coupled with the housing.

54. The apparatus of claim 31 wherein the housing is detachably coupled with the spaced alignment members of the body.

55. An apparatus for remotely and subcutaneously positioning a suture in tissue, wherein the apparatus comprises a body, an elongate member associated with and extending from the body, wherein a distal end of the elongate member includes an opening and wherein the opening is positioned to engage portions of the suture, a guide associated with the body and spaced from the elongate member, wherein the guide includes a key and wherein the key is positioned to align the suture with a longitudinal axis extending through the opening of the elongate member, and wherein the elongate member is coupled with a housing and wherein the housing is coupled with the body, a suture passing instrument having a shaft portion for passing the suture, wherein portions of the suture passing instrument are slidingly received by the key of the guide and in the opening of the elongate member, and wherein proximal portions of the suture passing instrument are coupled with an actuator for advancing and retracting the suture passing instrument within the guide, and a rod coupled with and extending between the actuator and the guide, for supporting the advancing and the retracting of the suture passing instrument within the guide.

56. The apparatus of claim 55 wherein the actuator is an arm coupled with the suture passing instrument and hingedly coupled with the body of the apparatus.

57. The apparatus of claim 55 which further includes a guard associated with and extending from the body.

58. The apparatus of claim 57 wherein the guide and the guard extend from opposing ends of the body.

59. The apparatus of claim 57 wherein the guard has an open region which is aligned with the axis of the opening, for receiving tip portions of the suture passing instrument.

60. The apparatus of claim 57 wherein the apparatus further includes a rod coupled with the suture passing instrument for supporting movements of the suture passing instrument within the guide, and wherein the guard has an open region which is aligned with a longitudinal axis extending through the rod, for receiving distal tip portions of the rod.

61. The apparatus of claim 57 wherein the guard is removably associated with the body.

* * * * *